(12) United States Patent
Antoniotti et al.

US007831392B2

(10) Patent No.: US 7,831,392 B2
(45) Date of Patent: Nov. 9, 2010

(54) SYSTEM AND PROCESS FOR VALIDATING, ALIGNING AND REORDERING ONE OR MORE GENETIC SEQUENCE MAPS USING AT LEAST ONE ORDERED RESTRICTION MAP

(75) Inventors: Marco Antoniotti, Jersey City, NJ (US); Bhubaneswar Mishra, Great Neck, NY (US); Thomas Anantharaman, DeForest, WI (US); Salvatore Paxia, New York, NY (US); David C. Schwartz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1582 days.

(21) Appl. No.: 10/432,766

(22) PCT Filed: Sep. 28, 2001

(86) PCT No.: PCT/US01/30426

§ 371 (c)(1),
(2), (4) Date: Oct. 5, 2005

(87) PCT Pub. No.: WO02/26934

PCT Pub. Date: Apr. 4, 2002

(65) Prior Publication Data

US 2006/0155483 A1    Jul. 13, 2006

Related U.S. Application Data

(60) Provisional application No. 60/293,254, filed on May 24, 2001, provisional application No. 60/236,296, filed on Sep. 28, 2000.

(51) Int. Cl.
*G01N 33/48* (2006.01)
*C12Q 1/68* (2006.01)
(52) U.S. Cl. ................................ 702/19; 702/20; 435/6
(58) Field of Classification Search ........................ None
See application file for complete search history.

(56) References Cited

U.S. PATENT DOCUMENTS 6,174,671 B1    1/2001    Anantharaman et al.

OTHER PUBLICATIONS

Anantharaman, T., et al., "Optical Mapping: A Complete System for Whole Genome Shotgun Mapping," Research Abstracts 2000 DOE Human Genome Program, Feb. 27-Mar. 2, 2000 Grantee Workshop in Santa Fee, NM, pp. 1-10.
Cai, Weiwen, et al., "High-resolution Restriction Maps of Bacterial Artificial Chromosomes Constructed by Optical Mapping," Proc. Natl. Acad. Sci. USA, vol. 95, Mar. 1998 Biochemistry, pp. 3390-3395/.
Gordon, David, et al., "*Consed*: A Graphical Tool for Sequence Finishing," Genome Research, 1998, vol. 8, pp. 195-202.

Richterich, Peter, "Estimation of Errors in 'Raw' DNA Sequences: A Validation Study," Genome Research, 1998, vol. 8, pp. 251-259.
Thompson, Julie D., et al., "A Comprehensive Comparison of Multiple Sequence Alignment Programs," Nucleic Acids Research, 1999, vol. 27, No. 13, pp. 2682-2690.
Morgenstern, Burkhard, et al., "Multiple DNA and Protein Sequence Alignment Based on Segment-to-Segment Comparison," Proc. Natl. Acad. Sci. USA, Oct. 1996, vol. 93, pp. 12098-12103.
Antoniotti, M. et al., "Genomics via Optical Mapping IV: Sequence Validation via Optical Map Matching," New York University Technical Report, TR2000-811, Mar. 2001, XP002433390.
Aston, C. et al., "Optical mapping and its potential for large-scale sequencing projects," *Trends in Biotechnology*, Elsevier, Amsterdam, NL, vol. 17, No. 7, Jul. 1999, pp. 297-302; XP004169729.
Plajzer-Frick, I. et al., "Optical Mapping as a Tool for Sequence Validation in Genomic Sequencing," Database Biosis [Online], Biosciences Information Service, Philadelphia, PA, US, Sep. 2000, XP002433393; and the International Genome Sequencing and Analysis Conference, vol. 12, Sep. 2000, pp. 83-84, 12th International Genome Sequencing and Analysis Conference, Miami Beach, FL, US.
Rouchka, E. et al., "Sequence Assembly Validation by Restriction Digest Fingerprint Comparison," Technical Report, Washington University Department of Computer Science, WUCS-97-40, [Online] 1997, XP002433391.

(Continued)

*Primary Examiner*—Shubo (Joe) Zhou
(74) *Attorney, Agent, or Firm*—Joseph T. Leone, Esq.; DeWitt Ross & Stevens S.C.

(57) ABSTRACT

A method and system are provided for comparing ordered segments of a first DNA restriction map with ordered segments of a second DNA restriction map to determine a level of accuracy the first DNA map and/or the second DNA map. In particular, the first and second DNA maps can be received (the first DNA map corresponding to a sequence DNA map, and the second DNA map corresponding to a genomic consensus DNA map as provided in an optical DNA map). Then, the accuracy of the first DNA map and/or the second DNA map is validated based on information associated with the first and second DNA maps. In addition, a method and system are provided for aligning a plurality of DNA sequences with a ordered DNA restriction map. The DNA sequences and the DNA map are received (the DNA sequences being fragments of a genome and the DNA map corresponding to a genomic consensus DNA map which relates to an optical ordered DNA map). Then, a level of accuracy of the DNA sequences and the DNA map is obtained based on information associated with the DNA sequences and the DNA map by means of the method and system described above. The locations of the DNA map at which the DNA sequences are capable of being associated with particular segments of the DNA map are located. Furthermore, it is possible to obtain locations of the DNA map (without the validation) by locating an optimal one of the locations for each of the DNA sequences for each of the locations.

38 Claims, 15 Drawing Sheets

OTHER PUBLICATIONS

Schwartz, D. et al., "Ordered Restriction Maps of *Saccharomyces cerevisiae* Chromosomes Constructed by Optical Mapping," Science, Oct. 1993, American Association for the Advancement of Science, US, pp. 110-114, XP002258437.

European Patent Office Search Report established May 20, 2007, for European patent application serial No. 01975549.5.

Anantharaman, T., et al., "Genomics via Optical Mapping III: Contiging Genomic DNA," ISMB-99 Proceedings, 1999, pp. 18-27, AAAI.

SYSTEM AND PROCESS FOR VALIDATING, ALIGNING AND REORDERING ONE OR MORE GENETIC SEQUENCE MAPS USING AT LEAST ONE ORDERED RESTRICTION MAP

CROSS-REFERENCE TO RELATED APPLICATIONS

This application is a national stage application of PCT Application No. PCT/US01/30426 which was filed on Sep. 28, 2001 and published on Apr. 4, 2002 as International Publication No. WO 02/26934 (the "International Application"). This application claims priority from the International Application pursuant to 35 U.S.C. §365. The present application also claims priority under 35 U.S.C. §119 from U.S. Patent Application Ser. Nos. 60/236,296 and 60/293,254, filed on Sep. 28, 2000 and May 24, 2001, respectively. The entire disclosures of these applications are incorporated herein by reference.

FIELD OF THE INVENTION

The present invention relates to a system and process for a sequence validation based on at least one ordered restriction map, and more particularly to validating, aligning and/or reordering one or more genetic sequence maps (e.g., ordered restriction enzyme DNA maps) using such ordered restriction map via map matching and comparison.

BACKGROUND INFORMATION

The sequence of nucleotide bases present in strands of nucleotides, such as DNA and RNA, carries the genetic information encoding proteins and RNAs. The ability to accurately determine a nucleotide sequence is crucial to many areas in molecular biology. For example, the study of genetics relies on complete nucleotide sequences of the organism. Many efforts have been made to generate complete nucleotide sequences for various organisms, including humans, mice, worms, flies and microbes.

There are a variety of well-known methods to sequence nucleotides, including the Sanger dideoxy chain termination sequencing technique and the Maxam-Gilbert chemical sequencing technique. However, the current technology limits the length of a nucleotide sequence that may be sequenced. Techniques have been developed to sequence larger nucleotide sequences. In general, these methods involve fragmenting the large sequence into fragments, cloning the fragments, and sequencing the cloned fragments. The sequences can be fragmented through the use of restriction enzymes or mechanical shearing. Cloning techniques include the use of cloning vectors such as cosmids, bacteriophage, and yeast or bacterial artificial chromosomes (YAC or BAC). The nucleotide sequence of the fragments can then be compared, overlapping regions identified, and the sequences assembled to form "contigs," which are sets of overlapping clones. By assembling the overlapping clones, it is possible to determine the sequence of nucleotide bases of the full length sequence. These methods are well known to those having ordinary skill in the art.

The accuracy of nucleotide sequence data is limited by numerous factors. For example, there may be missing sections due to incomplete representation of the genomic DNA. There may also be spurious DNA sequences intermixed with the desired genomic DNA. Common sources of contamination are vector-derived DNA and host cell DNA. Also, the accuracy of the identification of bases tends to degrade toward the end of long sequence reads. Additionally, repeated sequences can create errors in the re-assembly and/or the mismatching of contigs.

In order to reduce the sequence data errors, sequencing of the fragments is generally performed multiple times. To help reduce errors such as mismatching or misassembly resulting from repeated sequences, the "hierarchical shotgun sequencing" approach (also referred to as "map-based," "BAC-based" or "clone by clone") can be used. This approach involves generating and organizing a set of large insert clones covering the genome and separately performing shotgun sequencing on appropriately selected clones. Because the sequence information is local, the issue of long-range misassembly is eliminated and the risk of short-range misassembly is reduced.

Other known sequencing and characterization techniques involve generating restriction fragment fingerprints to determine whether close overlaps are present, thereby assembling the BACs into fingerprint clone contigs. Fingerprint clone contigs can be positioned along the chromosome by anchoring them with sequence-tagged sites (STS) markers from existing genetic and physical maps. These fingerprint clone contigs can be associated with specific STSs by probe hybridization or direct search of the sequenced clones. Clones can also be positioned by fluorescence in situ hybridization. Each of these known techniques are costly and time consuming.

Another approach for characterizing nucleotide sequences involves the use of ordered restriction maps of single molecules. One specific technique used to produce single molecule ordered restriction maps is "Optical Mapping". Optical mapping is a single molecule methodology for the rapid production of ordered restriction maps from individual DNA molecules. Ordered restriction maps are preferably constructed using fluorescence microscopy to visualize restriction endonuclease cutting events on individual fluorochrome-stained DNA molecules. Restriction enzyme cleavage sites are visible as gaps that appear flanking the relaxed DNA fragments (pieces of molecules between two consecutive cleavages). Relative fluorescence intensity (measuring the amount of fluorochrome binding to the restriction fragment) or apparent length measurements (along a well-defined "backbone" spanning the restriction fragment) have proven to provide accurate size-estimates of the restriction fragment and have been used to construct the final restriction map.

Such restriction map created from one individual DNA molecule is limited in its accuracy by the resolution of the microscopy, the imaging system (CCD camera, quantization level, etc.), illumination and surface conditions. Furthermore, depending on the digestion rate and the noise inherent to the intensity distribution along the DNA molecule, with some probability, one is likely to miss a small fraction of the restriction sites or introduce spurious sites. Additionally, investigators may sometimes (rather infrequently) lack the exact orientation information (whether the left-most restriction site is the first or the last). Thus, given two arbitrary single molecule restriction maps for the same DNA clone obtained this way, the maps are expected to be roughly the same in the following sense—if the maps are "aligned" by first choosing the orientation and then identifying the restrictions sites that differ by small amount, then most of the restrictions sites will appear roughly at the same place in both the maps.

For instance, in the original method, fluorescently-labeled DNA molecules were elongated in a flow of molten agarose containing restriction endonucleases, generated between a cover-slip and a microscope slide, and the resulting cleavage events were recorded by fluorescence microscopy as time-lapse digitized images. The second generation optical mapping approach, which dispensed with agarose and time-lapsed imaging, involves fixing elongated DNA molecules onto positively-charged glass surfaces, thus improving sizing precision as well as throughput for a wide range of cloning vectors (cosmid, bacteriophage, and yeast or bacterial artificial chromosomes (YAC or BAC)).

A DNA sequence map is an "in silico" order restriction map that is obtained for a nucleotide sequence by simulating a restriction enzyme digestion process. The sequence data is analyzed and restriction sites are identified in a predetermined manner. The resulting sequence map has some piece of identification data plus a vector of fragments, whose elements encode the size in base-pairs.

Sequenced clones can be associated with fingerprint clone contigs in the physical map by using the sequence data to calculate a partial list of restriction fragments in silico and comparing that list with the experimental database of BAC fingerprints. Genomic consensus maps are generated from optical maps using, e.g., "Gentig" software which is a conventional software that generates optical ordered restriction maps.

It was previously unknown how to determine the accuracy of the DNA sequence maps. Indeed such determination was either impossible or provided a small level of surety. It is one of the objects of the present invention to enable a validation of the DNA ordered sequence maps against the optical maps. Another object of the present invention is to enable an alignment and reordering of the DNA sequence maps based on the optical mapping.

Approaches to aligning or reconstructing restriction maps have been described in E. W. Myers et al., "An O(N2 lg N) Restriction Map Comparison and Search Algorithm", Bulletin of Mathematical Biology, 54(4):599-618, 1992; R. M. Karp et al., "Algorithms for Optical Mapping", RECOMB 98, 1998; Parida, L., A Uniform Framework for Ordered Restriction Map Problems, Journal of Computational Biology, Vol 5, No 4, Mary Ann Liebert Inc. Publishers, pp 725-739, 1998; Gusfield, D., Algorithms on Strings, Trees, and Sequences, Cambridge University Press, 1997; and Lee, J. K., Dancik, V., and M. S. Waterman, "Estimation for restriction sites observed by optical mapping using reversible-jump Markov Chain Monte Carlo", J. Comp. Biol., 5, 505-516, 1997. However, none of these publications disclose the novel processes and systems described herein below.

SUMMARY OF THE INVENTION

In general, an exemplary embodiment of the system and process for validating and aligning the simulated ordered restriction map against the optical ordered restriction map according to the present invention can be implemented as follows. First, each molecule may be cut in several places using a digestion process by one or more restriction enzymes as is known to those having ordinary skill in the art. Each of these "cut" molecules can represent a partial DNA (optical) ordered restriction map. Then, it is possible to reconstruct a complete Genome Wide (optical) ordered restriction map. Such reconstruction process can be carried out by an iterative process which maximizes the likelihood of a plausible hypothesis given the partial map and the model of the error sources (e.g., a Bayesian-based process).

It should be understood that the inputs to the Validation/Alignment system and process are preferably restriction maps (which include DNA sequences therein) and Genome wide (e.g. optical) ordered restriction maps (which can be represented as variable length vectors of segment/fragment information fields). Each segment information has two pieces of information associated therewith: size and standard deviation. The size may be a measure of the segment, which is proportional to the number of nucleotides present in the segment. The standard deviation preferably represents the error associated with the segment size measurement. Each map has associated therewith, e.g., two measures of how reliable the detection of cuts by the procedure is, i.e., the false positive probability and the digestion probability. The first measure relates to the event that the cut is detected incorrectly. The second measure relates to the event that the cut actually appears where it is reported.

According to the present invention, the optical and simulated ordered restriction maps are compared to one another to determine whether and to what extent they match. The accuracy of a match is computed by minimizing the error committed by matching one map against the other at a given position. An exemplary mathematical model and procedure underlying this computation is preferably a Bayesian-based procedure/algorithm. The computation is based on a Dynamic Programming Procedure ("DPP"). However, it should be understood that other procedures and algorithms can be utilized to compare to one another these maps to validate and align at least one such map, according to the present invention.

Using the Bayesian-based exemplary procedure with the system and method of the present invention, hypothesis can be obtained and the probability of a given event (based on the hypothesis) may be formulated. This probability is preferably a mathematical formula, which is then computed using a conventional model of various error sources. An exemplary optimization process which uses such formula may maximize or minimize the formula.

In order to find the extreme value of the overall probability formula over all possible combinations of matches, a conventional DPP can be used on the problem which was defined by the Bayesian-based exemplary procedure as described above. For example, the DPP may preferably compute a set of extreme values for a mathematical formula defined above by extending a partial solution in a predetermined manner while keeping track of a particular number of alternatives. All of the alternatives may be maintained in a table, and thus do not have to be recomputed every time the associated likelihood or score function needs to be evaluated.

Accordingly, a method and system according to the present invention are provided for comparing ordered segments of a first DNA map with ordered segments of a second DNA map to determine a level of accuracy the first DNA map and/or the second DNA map. In particular, the first and second DNA maps can be received (the first DNA map corresponding to a sequence DNA map, and the second DNA map corresponding to a genomic consensus DNA map as provided in an optical DNA map). Then, the accuracy of the first DNA map and/or the second DNA map is validated based on information associated with the first and second DNA maps.

In another embodiment of the present invention, the first DNA map and/or the second DNA map are validated by determining whether one or more matches exist between ordered segments of the first DNA map and the ordered segments of the second DNA map. In addition, a number of the matches which exist between the segments of the first DNA map and the segments of the second DNA map can be obtained.

In yet another embodiment of the present invention, the first DNA map and/or the second DNA map are validated by determining whether the first DNA map includes one or more cuts which are missing from the second DNA map. Also, a number and locations of the missing cuts based on the first and second DNA maps can be obtained thereafter.

According to a further embodiment of the present invention, the first DNA map and/or the second DNA map are validated by determining whether the second DNA map includes one or more cuts which are absent from the first DNA map. The validation can also be performed by determining whether the first DNA map includes one or more cuts which are missing from the second DNA map, obtaining a first number and locations of the missing cuts based on the first and second DNA maps, determining whether the second DNA map includes one or cuts which are absent from the first DNA map, and obtaining a second number and locations of the absent cuts based on the first and second DNA maps. Furthermore, it is possible to generate an error indication if the number of the matches is less than a match threshold, the first number of the missing cuts is greater than a first predetermined threshold, and/or the second number of the absent cuts is greater than a second predetermined threshold.

In another embodiment of the present invention, the first DNA map is an in-silico ordered restriction map obtained from a DNA sequence, which may include identification data and at least one vector of the segments of the first DNA map. At least one vector of the first segments can encode a size of base-pairs of the DNA sequence. Further, the second DNA map can include identification data and at least one variable-length vector representing its ordered segments.

In still another embodiment of the present invention, the second DNA map is defined as a subsequence of a genome-wide ordered restriction map. Also, the validation is performed by determining the accuracy of at least one of the first DNA map and the second DNA map using the following probability density function:

$$\Pr(D|\hat{H}(\sigma,p_c,p_f))$$

where D is the second DNA map, $\hat{H}$ is the first DNA map, $\sigma$ is a standard deviation summarizing map-wide standard deviation data, $p_c$ is a probability of a positive cut of a DNA sequence, and $p_f$ is a probability of a false-positive cut of the DNA sequence.

In another embodiment of the present invention, the accuracy can be validated as a function of an orientation of the first DNA map with respect to an orientation of the second DNA map. Also, the validation can be performed by executing a dynamic programming procedure ("DPP") on the first and second DNA maps to generate a first table of partial and complete alignment scores, and first auxiliary tables and first data structures to keep track of number and locations of cuts and segment matches, receiving a third DNA map which is a reverse map of the first DNA map, executing the DPP on the second and third DNA maps to generate a second table of partial and complete alignment scores, and second auxiliary tables and second data structures to keep track of number and locations of the cuts and the segment matches, analyzing a last row of the first table and a last row of the second table to obtain at least one optimum alignment of the first and second DNA maps, and reconstructing an optimum alignment and/or sub-optimal alignments using the first and second auxiliary tables and data structures.

According to still another embodiment of the present invention, the accuracy can be validated by matching an extension of one or more left end segment of the segments of the first DNA map to at least one segment of the second DNA map and/or by matching an extension of one or more right end segment of the segments of the first DNA map to at least one segment of the second DNA map. Furthermore, it is possible to detect an alignment of the first DNA map with respect to the second DNA map, the alignment being indicative of sequence positions of the segments of the first DNA map along the second DNA map.

In addition, other embodiments of the process and system according to the present invention are provided for aligning a plurality of DNA sequences with a DNA map. First, the DNA sequences and the DNA map can be received (the DNA sequences being fragments of a genome and the DNA map corresponding to a genomic consensus DNA map which relates to an ordered restriction—e.g. optical—DNA map). Then, a level of accuracy of the DNA sequences and the DNA map is validated based on information associated with the DNA sequences and the DNA map. The locations of the DNA map at which the DNA sequences are capable of being associated with particular segments of the DNA map are located. Furthermore, it is possible to obtain locations of the DNA map (without the validation) by locating an optimal one of the locations for each of the DNA sequences for each of the locations.

In another embodiment of the present invention, the locations are determined for each of the DNA sequences, they may be positions on the DNA map at which the corresponding DNA sequences are anchorable, and these locations can define at least one alignment of the DNA sequences with respect to the DNA map. The alignment may include multiple alignments of the DNA sequences with respect to the DNA map, and the multiple alignments may be ranked based on a predetermined criteria to obtain a score set which includes a particular score for each of the multiple alignments. The determination may be performed by providing the DNA sequences in a first order of the multiple alignments with respect to the DNA map and determining a position for each of the DNA sequences, with respect to the DNA map, by selecting the DNA sequences to be in a second order corresponding to the score set.

In still another embodiment of the present invention, the determination of the locations can be performed by restricting each of the DNA sequences to be associated with only one of the locations on the DNA map. Also, such determination may produce a single alignment of the DNA sequences with respect to the DNA map.

In yet another embodiment of the present invention, the determination can be performed by locating an optimal one of the locations for each of the DNA sequences to obtain an alignment solution for each of the locations. Also, the locating of the optimal location may be repeated for each subsequent one of the locations and excluding the alignment solution from a preceding locating procedure. Furthermore, each subsequent locating procedure can be made by relaxing at least one particular constraint to determine the respective locations. The particular constraint preferably includes a first requirement that two of the DNA sequences are prevented from overlapping when associated with the respective locations on the DNA map. The particular constraint can include a second requirement that a maximum number of the DNA sequences are associated with the respective locations on the DNA map, and a third requirement that an overall score of the alignment of the DNA sequences with respect to the locations on the DNA map is minimized or maximized. It is also possible to assign respective weighs to the second requirement and the third requirement.

BRIEF DESCRIPTION OF THE DRAWINGS

For a more complete understanding of the present invention and its advantages, reference is now made to the following description, taken in conjunction with the accompanying drawings, in which.

DETAILED DESCRIPTION

Figure 1:
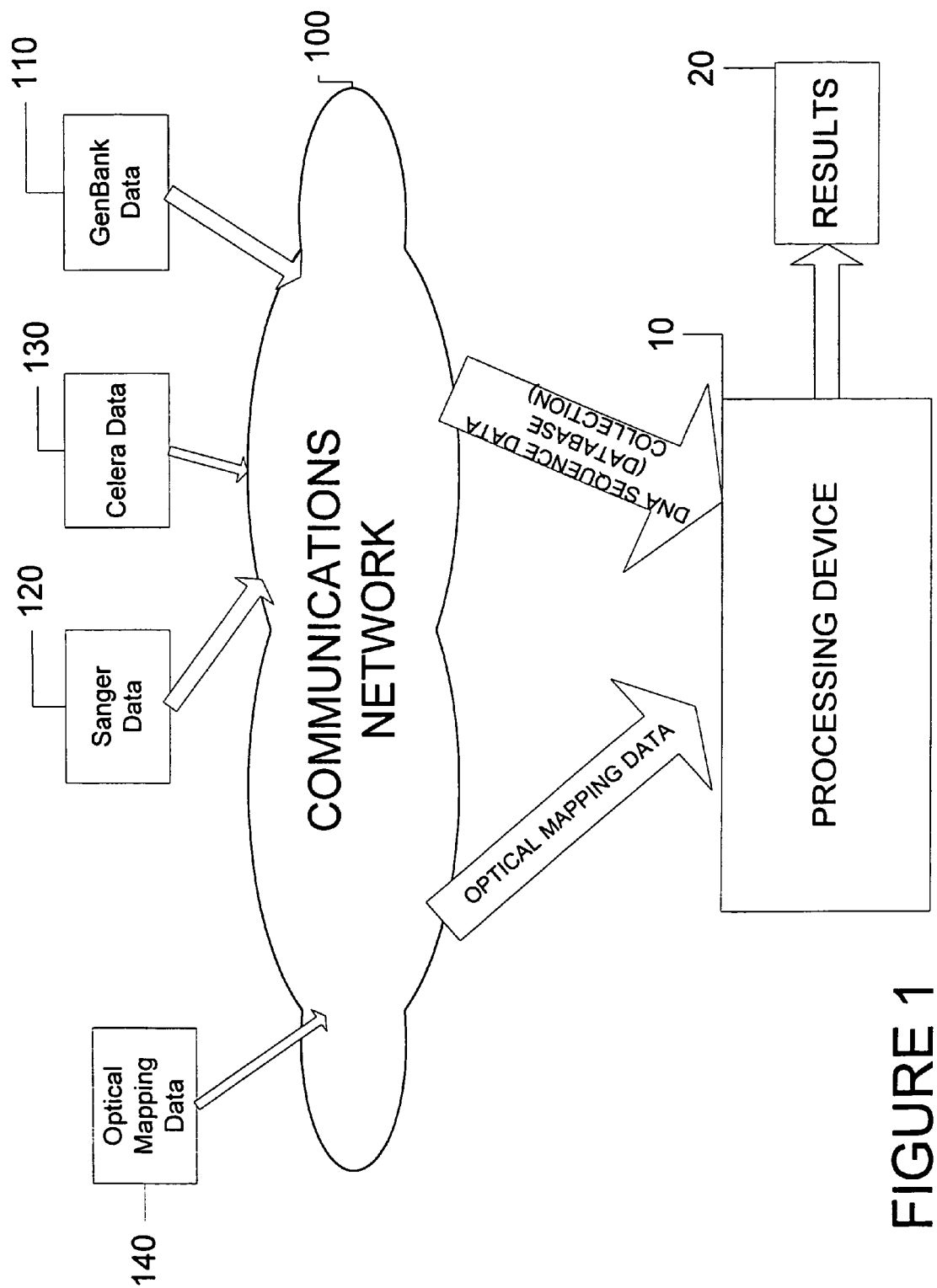
FIG. 1 is a first exemplary embodiment of a system for validating, aligning and/or reordering a genetic sequence using an optical map via map matching and comparison according the present invention.

FIG. 1 illustrates a first exemplary embodiment of a system for validating, aligning and/or reordering a genetic sequence using an optical (consensus) map via map matching and comparison according to the present invention. In this embodiment, the system includes a processing device 10 which is connected to a communications network 100 (e.g., the Internet) so that it can receive opticalsequence mapping data and DNA sequence data. The processing device 10 can be a mini-computer (e.g., "HEWLETT PACKARD"-brand mini computer), a personal computer (e.g., a "PENTIUM"-brand chip-based computer), a mainframe (e.g., "IBM"-brand 3090 system), and the like. The DNA sequence data can be provided from a number of sources. For example, this data can be "GENBANK"-brand Data 110 obtained from GenBank database (NIH genetic sequence database), Sanger Data 120 obtained from Sanger Center database, and/or "CELERA"-brand Data 130 obtained from the Celera Genomics database. These are publicly available genetic databases, or—in the last case—private commercial genetic databases. "Hewlett Packard" is a registered trade-mark of Hewlett-Packard Corporation (Palo Alto, Calif., USA), "Pentium" is a registered trade-mark of Intel Corporation (Santa Clara, Calif., USA), "IBM" is a registered trade-mark of International Business Machines Corporation (Armonk, N.Y., USA), "Celera" is a registered trade-mark of Celera Corporation (Alameda, California, USA). "GENBANK" is a registered trademark of the US Department of Health and Human Services (Bethesda, Md., USA). The optical sequence mapping data correspond to optical mapping data 140 that can obtained from external systems. For example, such optical map data, i.e., optical mapping ordered restriction data, can be generated using the methods described in U.S. Pat. No. 6,174,671. In particular, the methods described in this U.S. patent produce high-resolution, high accuracy ordered restriction maps based on data created from images of populations of individual DNA molecules digested by restriction enzymes.

Figure 2:
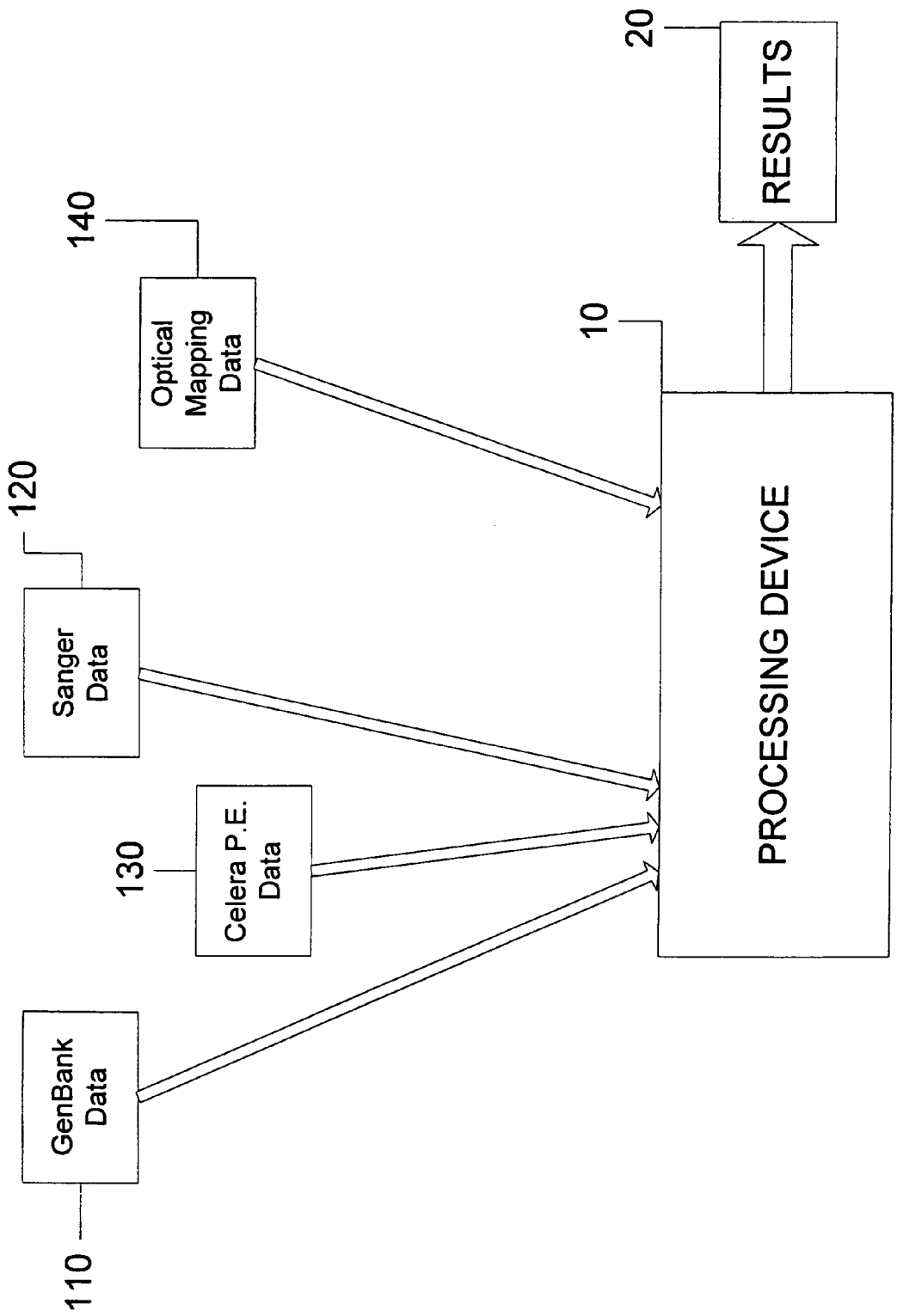
FIG. 2 is a second exemplary embodiment of a system for validating, aligning and/or reordering a genetic sequence using the optical map.

As shown in FIG. 1, after the processing device 10 receives the optical mapping data and the DNA sequence data via the communications network 100, it can then generate one or more results 20 which can be a validation/determination of the accuracy of the DNA sequence data and/or of the optical mapping data, an alignment of the DNA sequence data based on the results of the validation procedure, and reordering thereof FIG. 2 illustrates another embodiment of the system 10 according to the present invention in which the optical mapping data 140 is transmitted to the system 10 directly from an external source, without the use of the communications network 100 for such transfer of the data. In this second embodiment of the system as shown in FIG. 2, the DNA sequence data 110, 120, 130 is also transmitted directly from the one or more of the DNA sequence databases (e.g., the Sanger Center database, the Celera Genomics database and/or the GenBank database), without the need to use the communications network 100 shown in the first embodiment of FIG. 1. It is also possible for the optical mapping data 140 to be obtained from a storage device provided in or connected to the processing device 10. Such storage device can be a hard drive, a CD-ROM, etc. which are known to those having ordinary skill in the art.

A. Validation Process and System

General Flow Diagram

Figure 3:
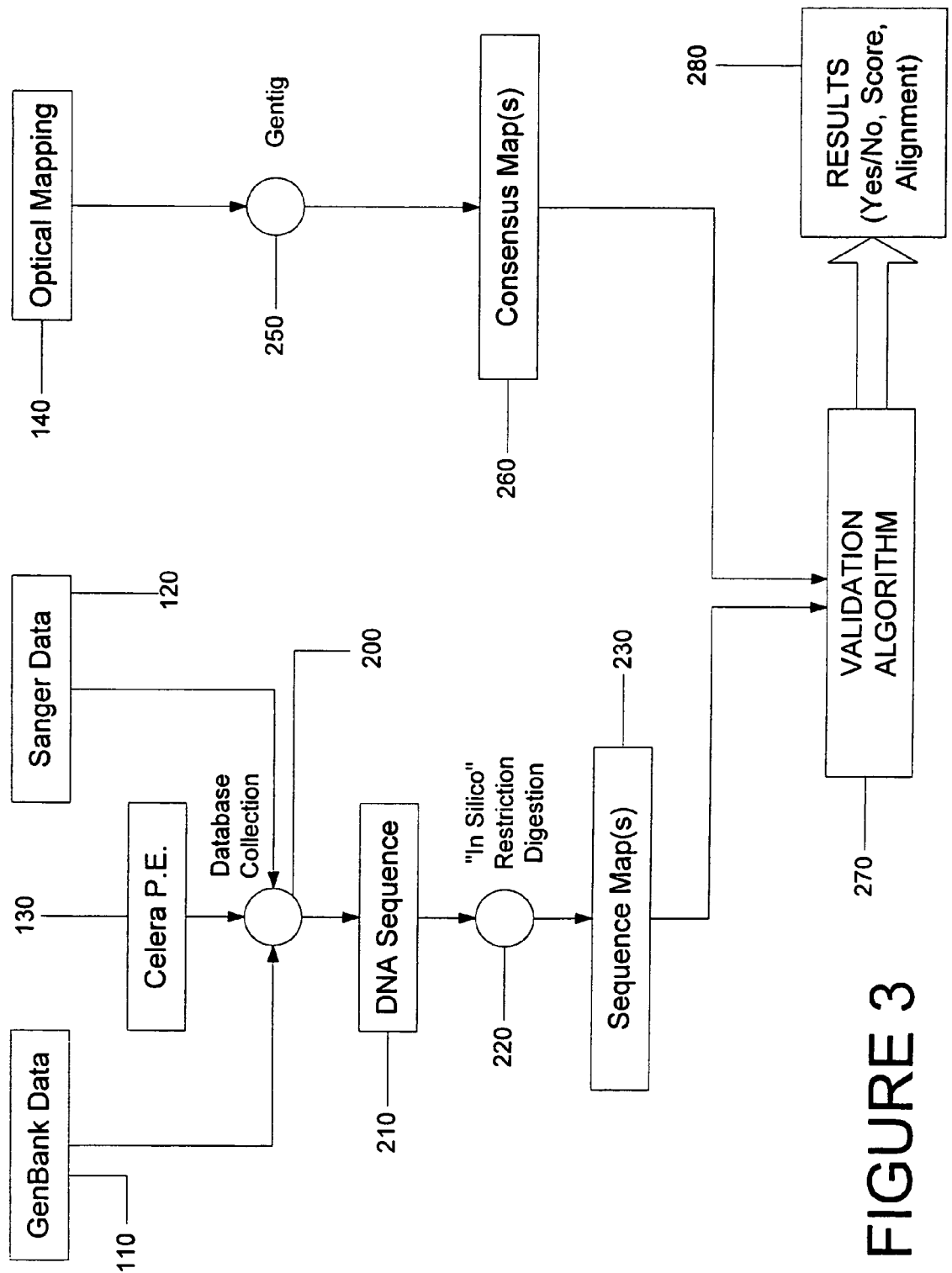
FIG. 3 is an exemplary embodiment of a validation procedure of a process according to the present invention.

FIG. 3 is an exemplary embodiment of the process according to the present invention which is preferably executed by the processing device 10 of FIGS. 1 and 2. In this exemplary embodiment, the optical mapping data 140 is forwarded to a technique 250 which constructs one or more consensus maps 260, based on this data 140 by considering the local variations among aligned single molecule maps. One example of such technique 250 is a "gentig" computer program as described in T. Anantharaman et al., "Genomics via Optical Mapping II: Ordered Restriction Maps", Journal of Computational Biology, 4(2), 1997, pp. 91-118, and T. Anantharaman et al., "Genomics via Optical Mapping III: Contiging Genomic DNA and Variations", AAAI Press, 7th International Conference on Intelligent Systems for Molecular Biology, ISMB 99, Vol. 7, 1999, pp. 18-27, the entire disclosure of which are incorporated herein by reference. In particular, "gentig" software uses a Bayesian-based (probabilistic) approach to automatically generate "contigs" from optical mapping data. For example, "contigs" can be assembled over whole microbial genomes. The "gentig" software repeatedly combines two islands that produce the greatest increase in probability density, excluding any "contigs" whose false positive overlap probability are unacceptable. For example, four parameters in the program can be altered to change the number of molecules that the program "contigs" together, thus forming the consensus maps. The details of the consensus maps shall be described herein below in further details.

According to the exemplary embodiment of the present invention, the DNA sequence data (e.g., the GenBank data 110, the Sanger data 120 and the Celera data 130) can be collected at a database collection junction 200, which can be a computer program executed by the processing device 10. This collection can be initiated and/or controlled either manually (e.g., by a user of the processing device 10 to obtain particular DNA sequences) and/or automatically using the processing device 10 or another external device. Upon the collection of the DNA sequence data from one or more of the DNA sequence databases 110, 120, 130, the database collection junction 200 outputs a particular DNA sequence 210 or a portion of such DNA sequence. Thereafter, the data for this DNA sequence 210 (or a portion thereof) is forwarded to a technique 220 which simulates a restriction enzyme digestion process to generate an "in silico" ordered restriction sequence map 230.

Thereafter, the system and process of the present invention executes a validation algorithm 270 which determines the accuracy of the ordered restriction sequence map 230 based on the data provided in the optical consensus map(s) 260. This result can be output as or more results 280 in the form of a response a score (e.g., a rank for each ordered restriction map), a binary output (e.g., the accuracy validated vs. unvalidated), etc.

Provided herein below is a detailed information regarding the consensus maps and the sequence maps.

Consensus (Optical) Map

The consensus optical map can be defined as a genome-wide, ordered restriction map which is represented as a structured item consisting of particular identification data and a variable length vector composed of fragments. For example, the consensus map can be represented by a vector of fragments, where each fragment is a triple of positive real numbers.

$$<c_i, l_i, \sigma_i> \epsilon R^3$$

and where $c_i$ is defined as the cut probability associated with a Bernoulli Trial, $l_i$ is the fragment size, related to the mean of a random variable with Gaussian distribution having an estimated standard deviation equal to $\sigma_i$. For example, the total length of the fragment vector as can be defined as N. Also, it is possible to define an index the vector of fragments from 0 to N−1.

The consensus maps can be created from several long genomic single molecule maps, where each molecule map thereof may be obtained from the images of the molecules stretched on a surface and further combined by a Bayesian algorithm implemented in the "gentig" program. As described above, the "gentig" program is capable of constructing consensus maps by considering local variations among the aligned single molecule maps.

Sequence Map

As is generally known, a sequence is a string of letters obtained from a set {A, C, G, T, N, X}. These letter have a standard meaning in the art if bio-informatics. In particular, the letters A, C, G, T are DNA bases, N is "unknown", and X is a "gap".

A sequence map is an "in silico" ordered restriction map obtained from the sequence by simulating a restriction enzyme digestion process. Hence, each sequence map has some piece of identification data plus the vector of fragments, whose elements encode exactly the size in base-pairs. The sequence map fragment vector j-th element is defined as a number $a_j$ which is the size of the fragment. The total length of the sequence map fragment vector is defined as M. The fragment vector is indexed from 0 to M−1.

Thus, each sequence map has at least a portion of identification data of the DNA sequence data 110, 120, 130, in addition to the vector of fragments whose elements encode exactly the size in base-pairs. The sequence map fragment vector j-th element is indicative of a number $a_j$ which corresponds to the size of the fragment. As an example, the total length of the ordered restriction sequence map fragment vector can be M. Thus, the fragment vector can be indexed from 0 to M−1.

Overall Process Description

Figure 4:
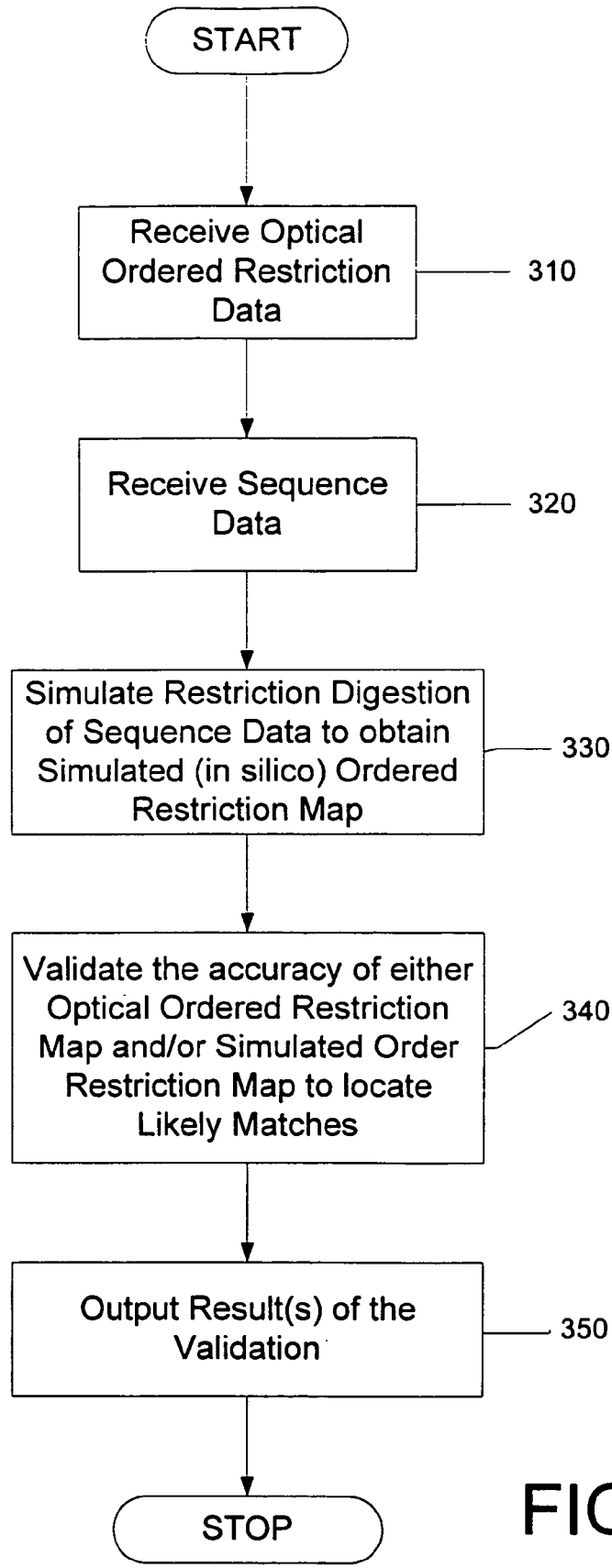
FIG. 4 is an exemplary embodiment of the process according to the present invention for simulating a restriction digestion of the sequence map, and then validating the accuracy of the consensus optical order restriction map and/or the simulated map.

FIG. 4 shows an exemplary flow chart of the embodiment of the process according to the present invention for simulating a restriction digestion of the sequence map, and then validating the accuracy of the consensus optical order restriction map and/or the simulated ordered map. This process can be performed by the processing device 10 which is shown in FIGS. 1 and 2. As shown in this flow chart, the processing device 10 receives the optical ordered restriction data in step 310, which can be the consensus optical map(s) 260 shown in FIG. 3. Then, in step 320, the processing device 10 receives the DNA sequence data, which is preferably the DNA sequence 210 which is also shown in FIG. 3. In step 330, the restriction digestion of the sequence data is simulated to obtain the simulated (in silico) ordered restriction map which is also shown in FIG. 3 as the sequence map(s) 230. Thereafter, in step 340, the accuracy of the optical ordered restriction map and/or of the simulated ordered restriction map is validated, preferably to locate likely matches within one another. Finally, the results of the validation are generated in step 350.

Exemplary Embodiment of Validation Procedure of the Exemplary Process

Figure 5A:
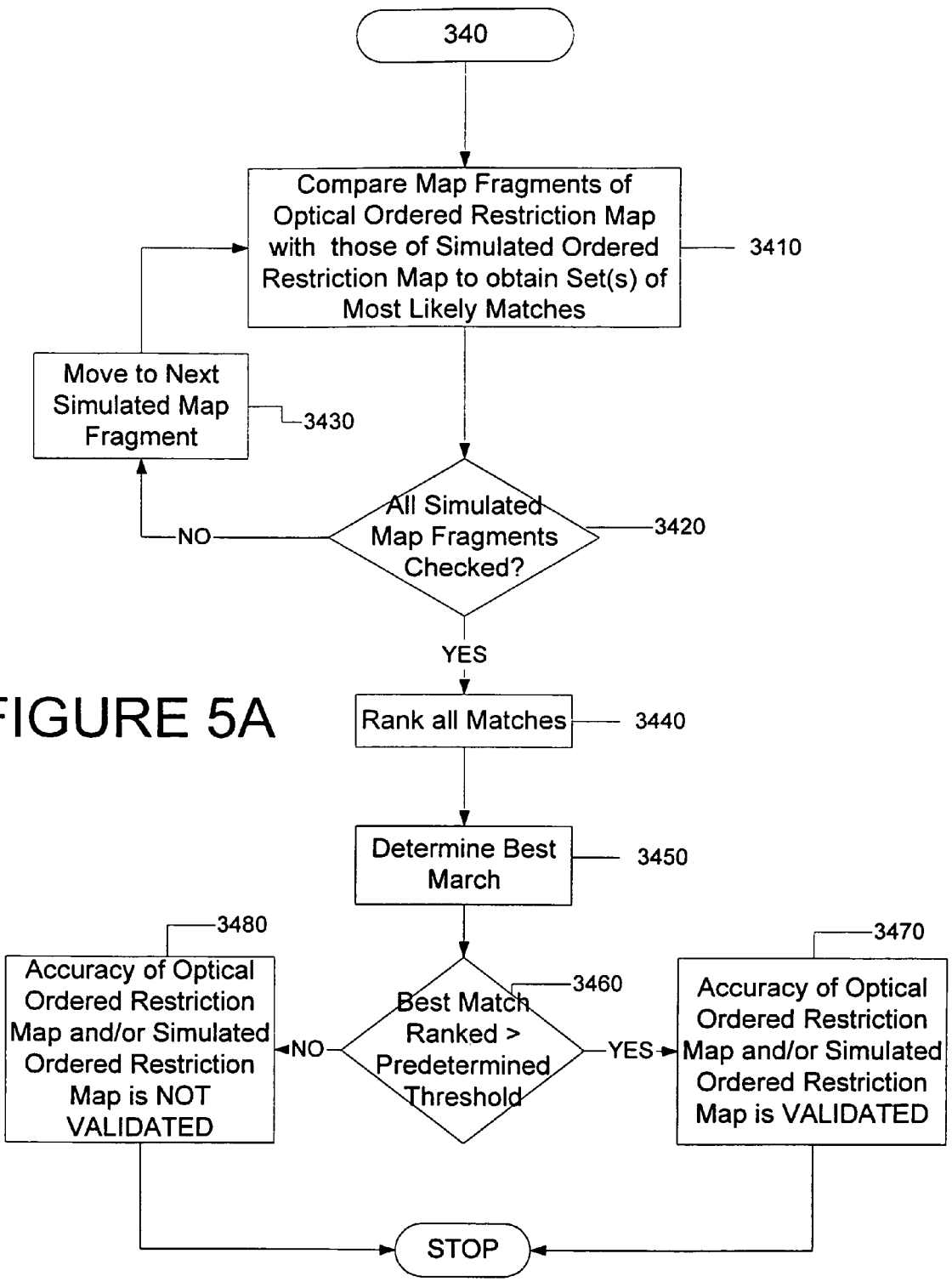
FIG. 5A is a detailed flow chart of an exemplary validation technique utilized in the process shown in FIG. 4.

FIG. 5A shows a detailed flow chart of an embodiment of the exemplary validation procedure utilized in step 340 of the process shown in FIG. 4. In particular, a current fragment of the optical ordered restriction map is compared to a respective fragment of the simulated ordered restriction map to obtain one or more set(s) of most likely matches (step 3410). Then, the processing device 10 determines if all fragments of the simulated ordered restriction map were checked in step 3420. If not, the process takes the next fragment of the simulated ordered restriction map to be the current fragment for checking performed in step 3430, and the comparison of step 3410 is repeated again for the current fragment of the simulated ordered restriction map. Otherwise, because it is determined that all fragments of the simulated ordered restriction map were checked, all of the matches are ranked in step 3440, and the processing device 10 determines the best match(es) in step 3450. If the processing device 10 determines that the rank of the best match(es) is greater than a predetermined threshold (step 3460), the processing device 10 validates the accuracy of the optical ordered restriction map and/or of the simulated ordered restriction map (step 3470). Otherwise such accuracy is not validated in step 3480. It should be understood that the exemplary validation procedure shown in FIG. 5A can be performed for one or multiple iterations over the fragments.

Figure 5B:
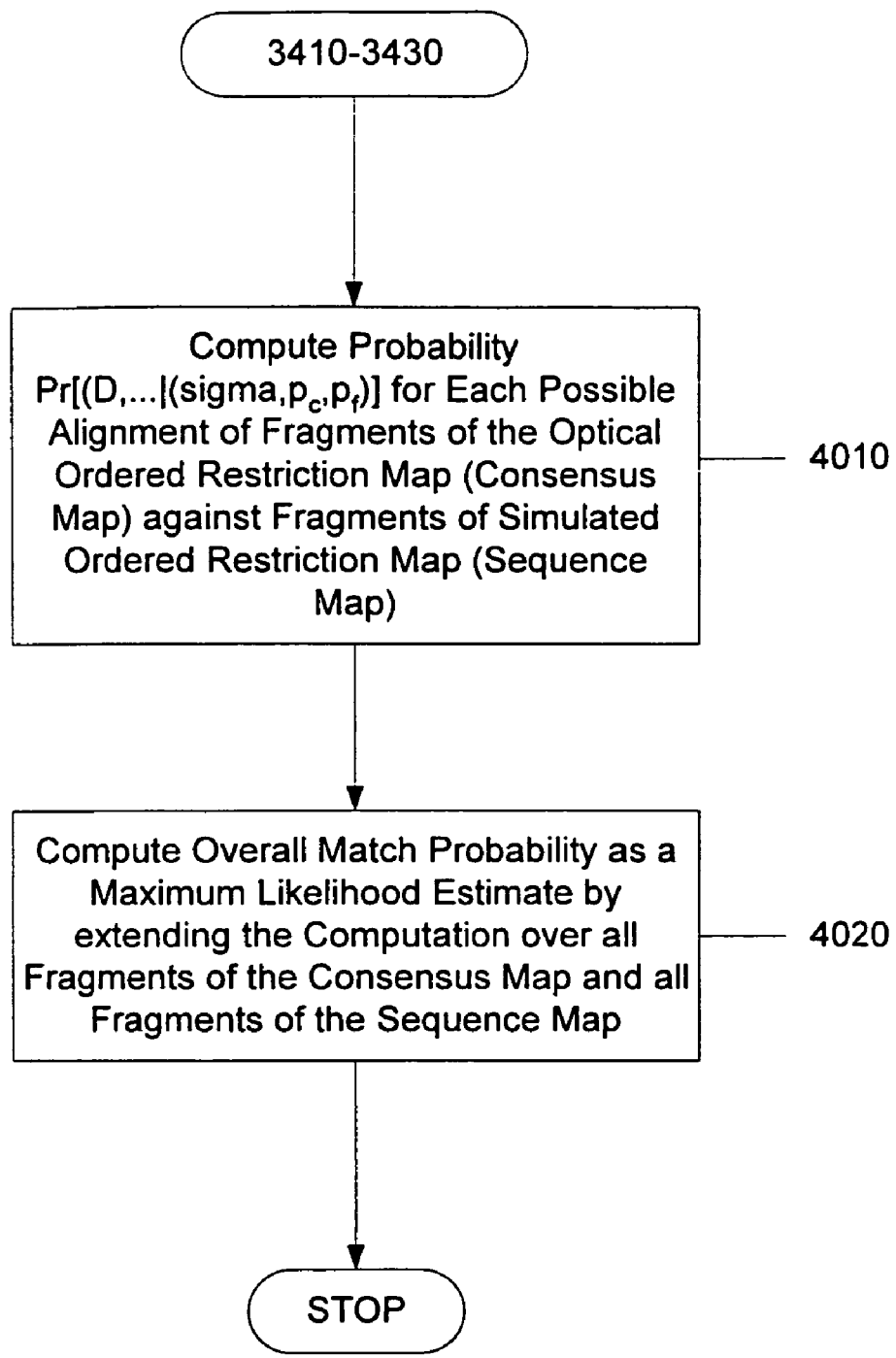
FIG. 5B is a detailed illustration of an exemplary flow diagram of particular steps of FIG. 5A in which fragments of the optical ordered restriction map are compared to fragment of the simulated ordered restriction map to obtain one or more set(s) of most likely matches.

FIG. 5B shows a detailed illustration of an exemplary flow diagram of steps 3410-3430 of FIG. 5A in which the fragments of the optical ordered restriction map are compared to the fragment of the simulated ordered restriction map to obtain one or more set(s) of most likely matches. Particularly, in step 4010, Probability $Pr(D|H(\sigma, p_c, p_f))$ as shall be described in further detail below, is calculated for each possible alignment of the fragments of the optical ordered restriction map (i.e., the consensus map) against fragments of simulated ordered restriction map (i.e., the sequence map). Then, in step 4020, an overall match probability as a maximum likelihood estimate ("MLE") is calculated by extending the computation over all fragments of the consensus map and all fragments of the sequence map.

The exemplary applications of the exemplary embodiment of the process according to the present invention on the sequence and consensus maps are provided in further detail below with reference to FIGS. 6A-6G.

Statistical Description of the Problem

Figure 6A:
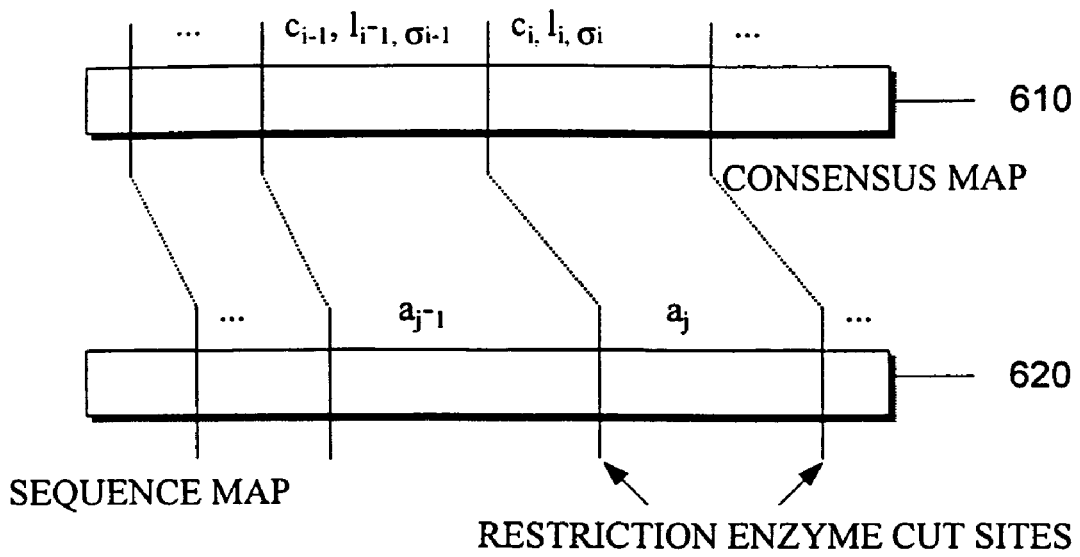
FIG. 6A is a first exemplary illustration of a technique for matching a sequence map against a consensus optical map.

FIG. 6A shows an exemplary setup of the matching procedure involving a sequence map (corresponding to the simulated ordered restriction map) and a consensus map (corresponding to the optical ordered restriction map). The sequence map is preferably considered to be an ideal map, i.e., viewed as the hypothesis H of a Bayesian problem to be analyzed, while the consensus map is preferably considered to be of data D to be validated against hypothesis H. In this manner the following probability density function is formed $Pr(D|H(\sigma,p_c,p_f))$, where σ is a standard deviation which summarizes maps wide standards deviation data (e.g., $\sigma=f(\sigma_i)$ for some function 'f'), $p_c$ is the cut probability, and $p_f$ is the false positive cut probability. This calculation is shown in FIG. 5b and discussed above.

Ideal Scenario

In an ideal scenario, the orientations of the sequence maps are known, there are no false cuts, and no missing cuts, i.e., $p_c=1$, and $p_f=0$, thus the terms associated with these parameters vanish, as it shall be described in further detail below. For example, if a position h in the consensus map is taken, the consensus map fragment sub-vector is provided from the position h to N−1. Also, the full fragment vector of the sequence map can be, e.g., from 0 to M−1. For the sake of simplicity of the explanation of the present invention, it is possible to remove the h position term of the consensus map fragment sub-vector, and count the consensus map fragments from the position term 0 so that expressions such as $l_i$, instead of $l_{h+i}$, can be utilized.

To obtain a "match" between the i-th fragments of the consensus map and the corresponding fragments of the sequence map, it is preferable to evaluate to what extent the consensus map and the sequence map deviate from one another. A Gaussian distribution should preferably be utilized for the i-th fragment of each of the maps, and the following expression may be evaluated:

$$\frac{1}{\sqrt{2\pi\sigma_i^2}} e^{-\frac{(l_i-a_j)^2}{2\sigma_i^2}}$$

Given the above expression, and with the assumption that the sequence map is correct (i.e., $Pr(H)=1$), the overall $Pr(D|H(\sigma, \ldots))$ function can be provided as:

$$Pr(D|H(\sigma, \ldots)) = \prod_{i=0}^{n} \left( \frac{1}{\sqrt{2\pi}\,\sigma_i} e^{-\frac{(l_i-a_j)^2}{2\sigma_i^2}} \right).$$

To maximize the likelihood of the validation, it is preferable to utilize the logarithm of the simplified expression and obtain the following expression:

$$\ln(Pr(D|H(\sigma, \ldots))) = \sum_{i=0}^{n} \ln\left(\frac{1}{\sqrt{2\pi\sigma_i^2}}\right) - \sum_{i=0}^{n} \left(\frac{(l_i-a_j)^2}{2\sigma_i^2}\right)$$

This express maximizes logarithmic likelihood, therefore it provides a Maximum Likelihood Estimate ("MLE").

Since it is possible to assume that the first term of the MLE does not vary extensively from one location to another, it is preferable to simplify the problem by minimizing a "weighted sum-of-error-square" cost function.

$$F(D) = \sum_{i=0}^{n} \left(\frac{(l_i-a_i)^2}{2\sigma_i^2}\right)$$

Minimizing function $F(D, \ldots)$ may yield the "best match" of the sequence map (represented as H) against the consensus map (represented as D).

According to the present invention, it is preferable to take into account the two possible orientations of the sequence map with respect to the consensus map. Below, false cuts and missing cuts in the consensus map are considered.

Orientation

Since the sequence map can be evaluated against the consensus map by "reversing" its orientation, the expression for Pr(D, σ, . . . |H) can be rewritten as:

$$Pr(D,|H(\ldots))=\max[Pr_1(D,|H(\ldots)),Pr_2(D|H^R(\ldots))],$$

where $H^R$ represents the reversed sequence map. As provided previously, it is possible to construct the function F as:

$$F(D,H)=\max[F_1(D,H),F_2(D,H^R)].$$

Thus, the expression for $F_2(D, H^R)$ will be as follows:

$$F_2(D, H^R) = \sum_{i=0}^{n} \left( \frac{(l_i - a_{(n-i)})^2}{2\sigma_i^2} \right)$$

False Cuts and Missing Cuts

In order to correctly model errors in the matching process, it is preferable to take into account false cuts and missing cuts. For example, the matching process can be modeled with two parameters:

Missing restriction sites in the sequence map are preferably modeled by a probability $p_c$ (i.e., a "cut" probability). In particular, $p_c=1$ means that the restriction sites are actually present in the map, $0 \leq p_c < 1$ means that there are some missing cuts, etc.

False restriction sites in the consensus map are preferably modeled by a rate parameter $p_f$ (i.e., a "false" cut probability). In an exemplary case, $0 < p_f \leq 1$ means that the consensus map may have some false cuts.

These parameters should preferably be included in the expression describing Pr( . . . ) and, therefore in the function F( . . . ) described above.

Example 1

Figure 6B:
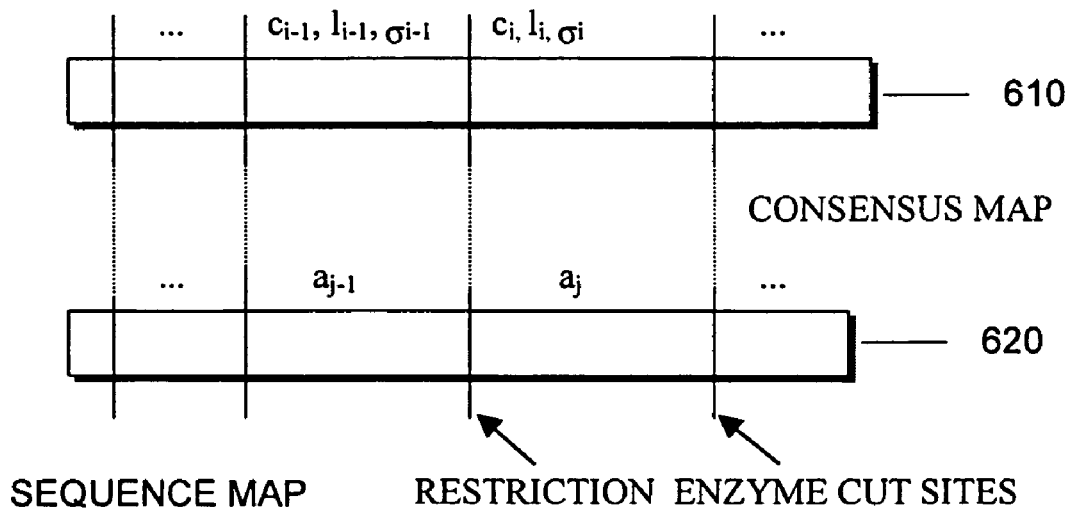
FIG. 6B is a second exemplary illustration of the technique for matching the sequence map against the consensus optical map in which the consensus optical map does not possess any false enzyme cuts and the sequence map does not have any missing enzyme cut(s)

No missing cuts and no false cuts. In this example as shown in FIG. 6B, the term for the matching of the i-th fragment of the sequence map 610 against the i-th fragment of the consensus map 620 should preferably take into account the cut probability $p_c$. Thus, the expression is as follows:

$$p_c \times \frac{1}{\sqrt{2\pi\sigma_i^2}} e^{-\frac{(l_i - a_j)^2}{2\sigma_i^2}}.$$

which yields the cost function, after taking the negative log likelihood.

$$\ln\left(\frac{\sqrt{2\pi\sigma_i^2}}{p_c}\right) + \frac{(l_i - a_j)^2}{2\sigma_i^2}.$$

Example 2

Figure 6C:
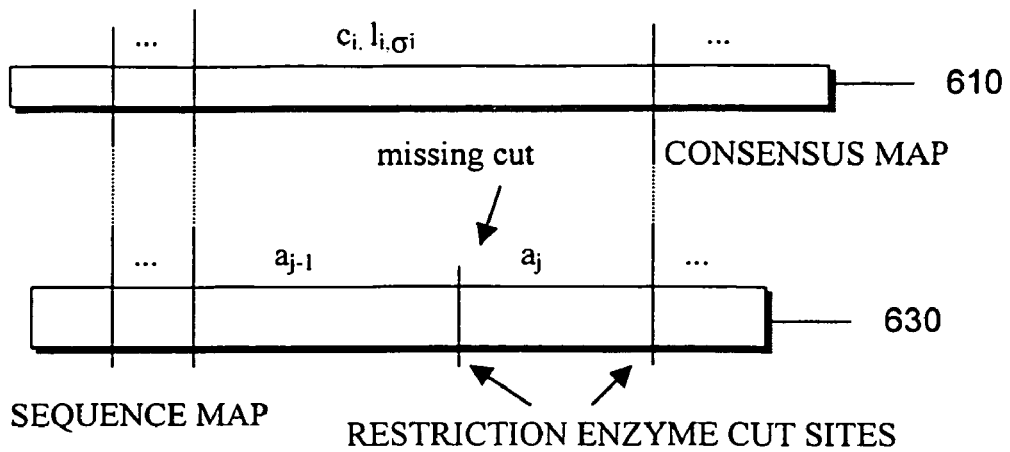
FIG. 6C is a third exemplary illustration of the technique for matching the sequence map against the consensus optical map in which the consensus optical map does not possess any false enzyme cuts while the sequence map is missing the enzyme cut(s)

Missing cuts and no false cuts. In this example and as shown in FIG. 6C, the exemplary embodiment of the system and method of the present invention considers a cut in the sequence map 630 that has no corresponding cut in the consensus map 610. A match is attempted of the i-th consensus map fragment against the aggregation of the j and j−1 fragments in the sequence map 630. For example, the computation of the Gaussian expression should be "penalized" by taking into account the missing cut. The main term is preferably modeled as:

$$p_c \times \frac{1}{\sqrt{2\pi\sigma_i^2}} e^{-\frac{(l_i - (a_j + a_{(j-1)}))^2}{2\sigma_i^2}} \times (1 - p_c).$$

yielding a cost function:

$$\ln\left(\frac{\sqrt{2\pi}\,\sigma_i}{p_c}\right) + \frac{(l_i - (a_j + a_{(j-1)}))^2}{2\sigma_i^2} + \ln\left(\frac{1}{1 - p_c}\right).$$

Example 3

Figure 6D:
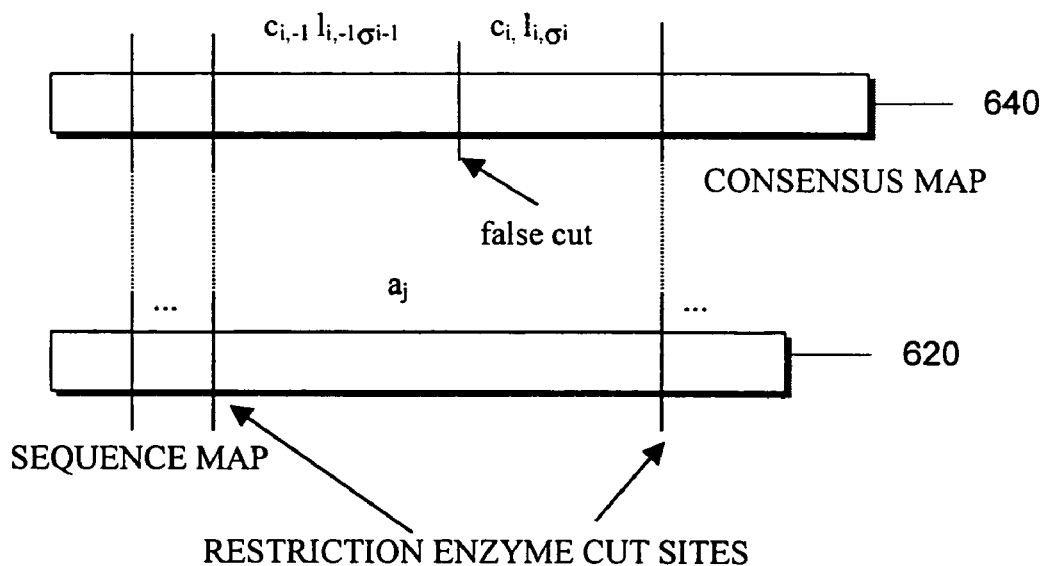
FIG. 6D is a fourth exemplary illustration of the technique for matching the sequence map against the consensus optical map in which the consensus optical map has a false enzyme cut and the sequence map does not have any missing enzyme cuts.

No missing cuts and some false cuts. In this case and as shown in FIG. 6D, the converse case of Example 2 is being considered. A false cut event of the consensus map 640 can be modeled as a Bernoulli trial with probability $p_f$. For example, the full term for such matching would likely aggregate fragments i and i−1 of the consensus map 640 against the j-th fragment of the sequence map 620. The full term would likely be:

$$p_c \times \frac{1}{\sqrt{2\pi(\sigma_i^2 + \sigma_{(i-1)}^2)}} e^{-\frac{((l_i + l_{(i-1)}) - a_j)^2}{2(\sigma_i^2 + \sigma_{(i-1)}^2)}} \times p_f.$$

Taking the negative log likelihood again, the following expression is obtained:

$$\ln\left(\frac{\sqrt{2\pi(\sigma_i^2 + \sigma_{(i-1)}^2)}}{p_c}\right) + \frac{((l_i + l_{(i-1)}) - a_j)^2}{2(\sigma_i^2 + \sigma_{(i-1)}^2)} + \ln\left(\frac{1}{p_f}\right).$$

It should be noted that for the current data obtained from the optical mapping process, $p \simeq 10^{-5}$. This current data often dominate the complete expression.

Example 4

Figure 6E:
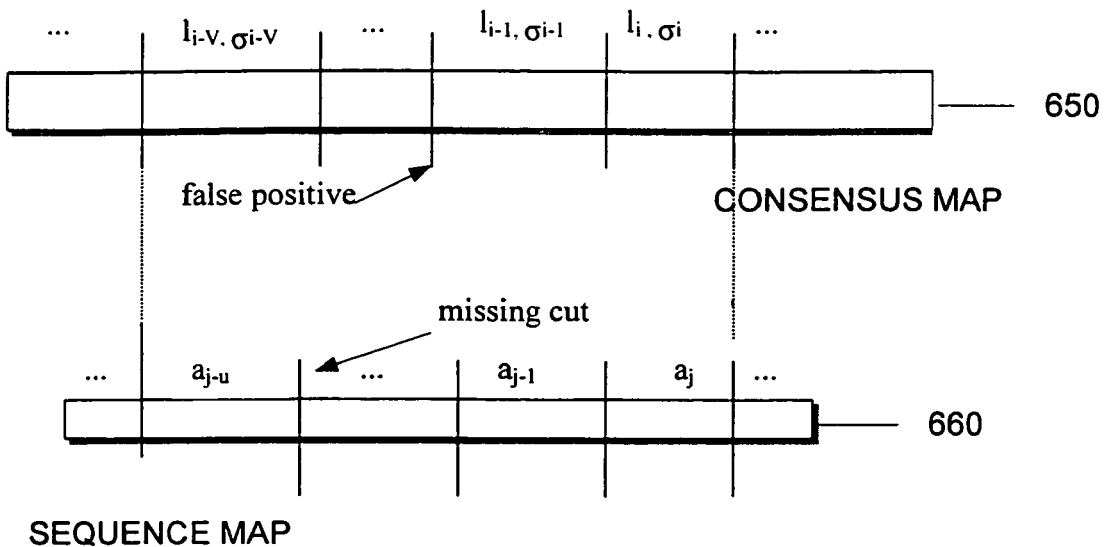
FIG. 6E is a fifth exemplary illustration of the technique for matching the sequence map against the consensus optical map in which the consensus optical map has a false enzyme cut and the sequence map is missing the enzyme cut.

Some missing cuts and some false cuts. Of course, it is conceivable that there may be missing cuts and false cuts together as shown in FIG. 6E. It is possible to accurately match or align the i−u cut in the sequence map 660 against the j−v cut in the consensus map 650. It is also possible to properly match the (i+1)-th cut (the cut immediately following the i-th fragment in both the consensus map 650 and the sequence map 660) in the two maps by appropriately treating all the intervening missing cuts in sequence map 660 and all the intervening false cuts in the consensus map 650. In this case, the "matching term" has the following general form:

$$p_c \times \frac{1}{\sqrt{2\pi(\sigma_i^2 + \sigma_{(i-1)}^2 + \ldots + \sigma_{(i-v)}^2)}} \times$$

$$e^{\left(-\frac{((l_i + l_{(i-1)} + \ldots + l_{(i-v)}) - (a_j + a_{(j-1)} + \ldots + a_{(j-u)}))^2}{2(\sigma_i^2 + \sigma_{(i-1)}^2 + \ldots + \sigma_{(i-v)}^2)}\right)} \times (1 - p_c)^{(u-1)} \times p_f^{(v-1)}.$$

Taking the negative log likelihood, the following expression is obtained:

$$-\ln p_c + \ln\left(\sqrt{2\pi(\sigma_i^2 + \sigma_{(i-1)}^2 + \ldots + \sigma_{(i-v)}^2)}\right) +$$

$$\frac{((l_i + l_{(i-1)} + \ldots + l_{(i-v)}) - (a_j + a_{(j-1)} + \ldots + a_{(j-u)}))^2}{2(\sigma_i^2 + \sigma_{(i-1)}^2 + \ldots + \sigma_{(i-v)}^2)} +$$

$$(u-1)\ln\frac{1}{1-p_c} + (v-1)\ln\frac{1}{p_f}.$$

B. Dynamic Programming Procedure

The validation of a sequence map against the optical map can be implemented as a dynamic programming procedure ("DPP"). Detailed descriptions of the DPP are provided in T. H. Cormen et al., "Introduction to Algorithms", The MIT Press and McGraw-Hill, 1990, and D. Gusfield, "Algorithms on Strings, Trees, and Sequences", Cambridge University Press, 1997, the entire disclosures of which is incorporated herein by reference. An exemplary DPP for the process according to the present invention is as follows:

Procedure sequence-map-validate (sequence-map, consensus-map)/*Other parameters will be specified . . . e.g., $p_f$, $p_c$, k, etc. */begin
        run DPP on consensus-map and sequence map;
        run DPP on consensus-map and reversed sequence map;
        collect the k "best" alignments by examining the last row of both DPP tables and "return" them;
    end This DPP procedure can be executed two or more times. It is improbable for two alignments for the sequence map and for its reversed version to have equivalent scores. It is preferable to start from the DPP's main recurrence to obtain a formulation of the sequence map vs. consensus map matching expression.

Dynamic Programming "Main" Recurrence

For the description provided below, index i shall be used to indicate a fragment in the consensus map, and the index j to indicate a fragment in the sequence map. Assuming that the consensus map has M fragments and that the sequence map has N fragments, the DPP may preferably utilize a N×M matching table T. Considering the entry T[i, j], this entry will likely contain the partially computed value of the matching function F( . . . ). For example, F( . . . ) would be incrementally computed from "left" to "right" by taking into consideration all possible fragment by fragment matches.

The main recurrence for entry T[i, j] is provided as follows:

$$T[i,j] := \min_{\substack{0 < u \leq i \\ 0 < v \leq j}} \left( \begin{array}{l} T[i-u, j-v] + \ln\left(\frac{\sqrt{2\pi(\sigma_i^2 + \sigma_{(i-1)}^2 + \ldots + \sigma_{(i-v)}^2)}}{p_c}\right) + \\ \frac{((l_i + l_{(i-1)} + \ldots + l_{(i-v)}) - (a_j + a_{(j-1)} + \ldots + a_{(j-u)}))^2}{2(\sigma_i^2 + \sigma_{(i-1)}^2 + \ldots + \sigma_{(i-v)}^2)} + \\ (u-1)\ln\frac{1}{1-p_c} + (v-1)\ln\frac{1}{p_f} \end{array} \right).$$

The determination of the respective sizes of u and v should be performed. In one exemplary embodiment of the present invention, the sizes of u and v should preferably depend on $\sigma_i$'s. In another exemplary embodiment of the present invention, u and v may depend also on the digestion rate of the "in vivo" experiment that breaks up the DNA molecule. However, a pragmatic bound may be equal to, e.g., three times the overall standard deviation (which in practice can be approximated by the value 3). This bound may preferably become a parameter of the DPP. In this way, the computation for each entry T[•,•] should consider approximately nine neighboring or adjacent entries.

A simple model for the initial conditions should preferably be as follows:

$T[i,0] := \infty$, for $i \in [1,N]$.

$T[i,0] := 0$, for $j \in [1,M]$

In this model, it is preferably to never match or strongly penalize a match of the first fragments of the consensus map against an "inner" fragment of the sequence map (cf. first column having a ∞ value). Also, the match of any fragment of the consensus map can be made against the first fragment of the sequence map rather neutral (with the first two zero values). A more complex model initializes the first row of the dynamic programming table by taking into account, e.g., only the size of the i-th fragment. Provided below is an exemplary description of a complete model for the above-referenced boundary conditions.

Left and Right End Fragment Computations.

It is possible to provide a more sophisticated and accurate model for the left fragments and right fragments calculations (i.e. for the initial and final conditions). Such models take into consideration the case in which certain fragments on either the left or the right of the sequence map do not "properly match" any fragment in the consensus map.

I. Left End Penalty Computation

Figure 6F:
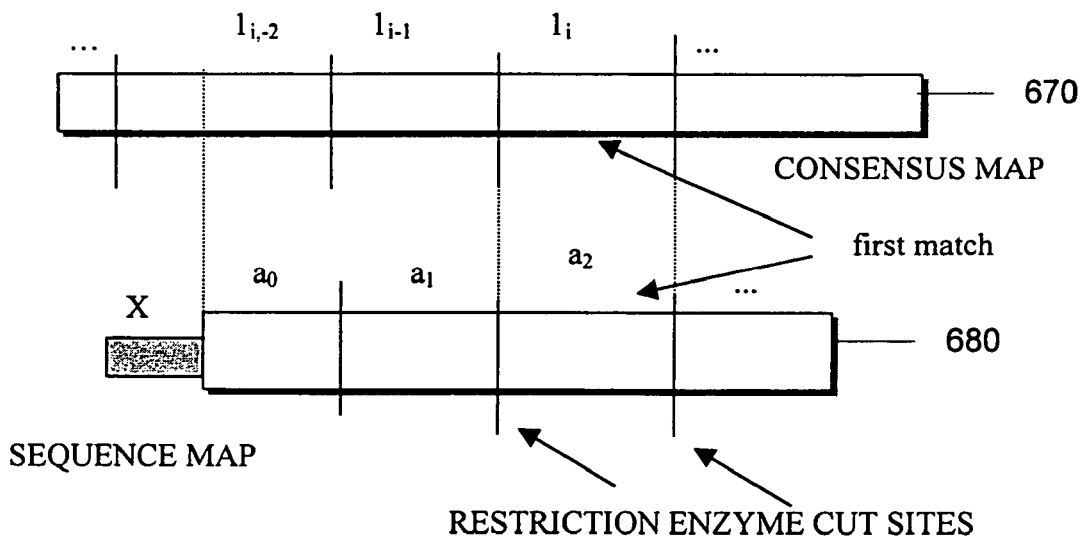
FIG. 6F is a sixth exemplary illustration of the technique for matching the sequence map against the consensus optical map in which left fragments of each of the consensus optical and sequence maps are mismatched.

As shown in FIG. 6F, the first "matching fragments" are $a_2$ from the sequence map 680, and $l_j$ from the consensus map 670, identified by their size. The general case is for fragment i of the sequence map 680 to match fragment j of the consensus map 670.

An analysis of the fragment $\alpha_0$ of the sequence map 680 is as follows. Most of the time, the left end of this fragment $\alpha_0$ (which can assume not to be corresponding to an actual restriction site) will fall within the boundaries of fragment i–n of the consensus map 670 (for $0 \leq n \leq i$).

Within this framework, the minimum value that can be assigned to a "match" of the left end fragments of the sequence map 680 corresponds to one of three cases:

Match by extension of the first left end fragment of the sequence map 680.

Bad matches until fragment i of the sequence map matches fragments j of the consensus map 670.

Match without extension to some fragment in the consensus map 670.

Example 1

Extending $\alpha_0$ by x leads to a match. If $\alpha_0$ is "extended" by an extra size x (as shown in FIG. 6F), x is extended as far to the left as possible to match the cut on the left of fragments i–n (e.g., fragment of size $l_{i-2}$ illustrated in FIG. 6F).

The value of this match (which is built on top of the derivation performed for the "regular case") is provided by the following expression:

$$\ln\left(\frac{\sqrt{2\pi(\sigma_{(i-n)}^2 + \sigma_{(i-(n-1))}^2 + \ldots + \sigma_i^2)}}{p_c}\right) +$$

$$\frac{((l_{(i-n)} + l_{(i-(n-1))} + \ldots + l_i) - (x + a_0 + a_1 + \ldots + a_j))^2}{2(\sigma_{(i-n)}^2 + \sigma_{(i-(n-1))}^2 + \ldots + \sigma_i^2)} +$$

$$\frac{x}{L} + (n-1)\ln\frac{1}{p_f} + j\ln\frac{1}{1-p_c}.$$

This case express depends on two parameters which did not appear in the regular case:

x being the size extension (please note it in the second and the third term), and L being the molecule map average fragment size.

The second sub-term is preferably the regular "sizing error" penalty which takes into account the extension x. The third sub-term may add an extra penalty based on the amount of the end fragment being stretched with respect to the overall structure of the expression. To utilize the expression, it is beneficial to find where its minimum with respect to the position of x. By differentiating in this manner, the expression can be minimized by setting x as follows:

$$x = ((l_{(i-n)} + l_{(i-(n-1))} + \ldots + l_i) - (a_0 + a_1 + \ldots + a_j)) -$$

$$\frac{(\sigma_{(i-n)}^2 + \sigma_{(i-(n-1))}^2 + \ldots + \sigma_i^2)}{L}$$

By substituting this value for x in the original expression, the following expression is obtained:

$$\ln\left(\frac{\sqrt{2\pi(\sigma_{(i-n)}^2 + \sigma_{(i-(n-1))}^2 + \ldots + \sigma_i^2)}}{p_c}\right) +$$

$$\frac{((l_{(i-n)} + l_{(i-(n-1))} + \ldots + l_i) - (a_0 + a_1 + \ldots + a_j))}{L} +$$

$$\left(-\frac{1}{2L^2}\right)(\sigma_{(i-n)}^2 + \sigma_{(i-(n-1))}^2 + \ldots + \sigma_i^2) + n\ln\frac{1}{p_f} + j\ln\frac{1}{1-p_c}.$$

Again, the last two sub-terms may account for the false cuts and the missing cuts, respectively. It is possible to assume that there is at least one "good" cut in the sequence map.

Example 2

No extension and bad matches until i and j. In this case, the first "good match" is located when fragment i of the sequence map matches fragments j of the consensus map. The expression corresponding to this case is $$n\ln\left(\frac{1}{p_f}\right) + (j+1)\ln\left(\frac{1}{1-p_c}\right)$$

This expression takes into consideration (and possibly corrects) all missing matches and the false matches in both maps (e.g., the j+1 term takes into account the 0-th cut as a missing cut).

Case 3: Match without extension to some fragment in the consensus map. It shall be assumed that a "good match" exists between fragment i of the consensus map and fragments j of the sequence map, and, as with Example 1 of this subsection, the fragment from the consensus map (which is within which the end of fragment 0— size $\alpha_0$—of the sequence map lies) is indexed i–n.

A match of the fragment 0 of the sequence map to any of the n fragments up to fragment i of the consensus map as then attempted. All possible missing cuts and false cuts along the way are taken into consideration. The attempt of minimizing the following expression (dependent on k) will likely compete against the expressions in Examples 1 and 2 for the best end match.

$$\min_{0 \leq k \leq i}\left(\frac{((l_{(i-k)} + l_{(i-(k-1))} + \ldots + l_i) - (x + a_0 + a_1 + \ldots + a_j))^2}{2(\sigma_{(i-k)}^2 + \sigma_{(i-(k-1))}^2 + \ldots + \sigma_i^2)} + (k-1)\ln\frac{1}{p_f} + j\ln\frac{1}{1-p_c}\right).$$

II. Right End Penalty Computation

Figure 6G:
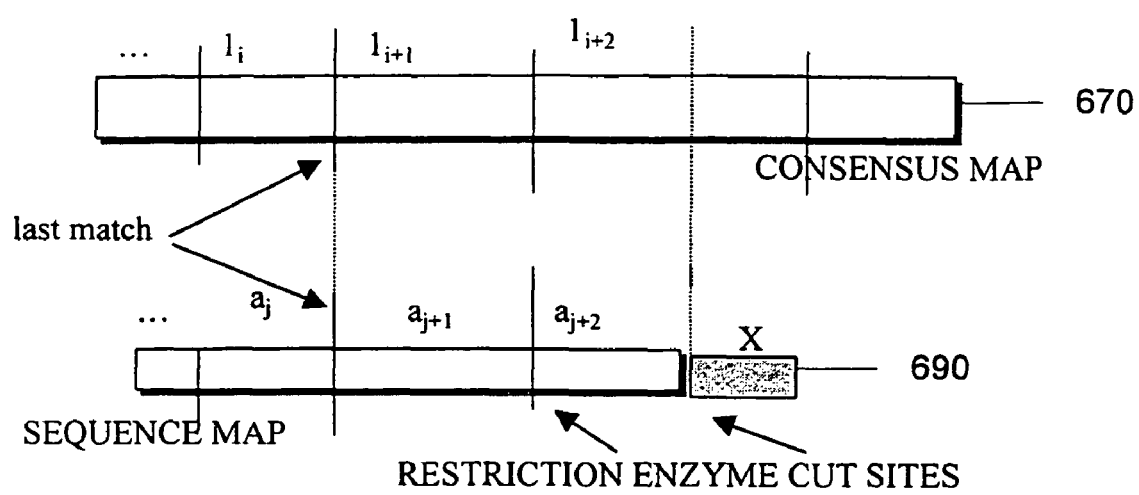
FIG. 6G is a sixth exemplary illustration of the technique for matching the sequence map against the consensus optical map in which right fragments of each of the consensus optical and sequence maps are mismatched.

FIG. 6G shows an exemplary illustration of the maps which are utilized for the right end penalty computation, i.e., for fragments trailing the end of the sequence map 690 and/or of the consensus map 680. This computation is almost symmetric to the left end penalty computation described above.

However, there is a difference to be taken into account for the right end computation which makes the computation asymmetrical with respect to the left end penalty computation described above. When the "last good match" between fragment i of the consensus map 670 and fragment j of the sequence map 690 is considered, a consideration of what is the score of the match up to that point should also be undertaken. In particular, the value T[, i] should be considered (thus assumed to be available at that point).

Thus, as per the left end computation, three terms should be considered. They are analogous to the three terms for the left end computation, but they should be augmented with T[j, i] to be meaningful.

III. Description of the Exemplary Validation Procedure

Figure 7:
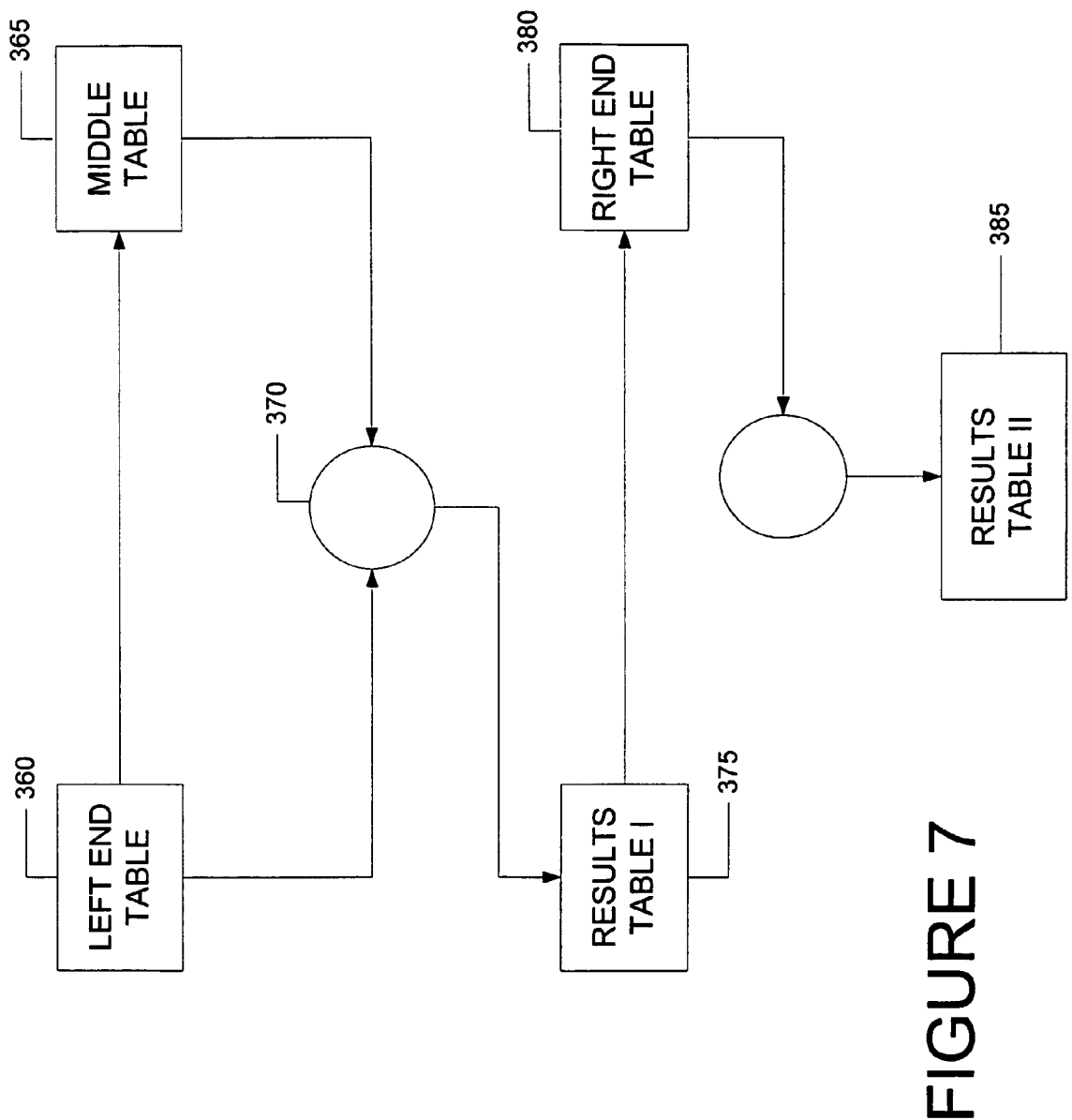
FIG. 7 is a detailed illustration of the exemplary flow diagram of the validation procedure according to the present invention which utilizes dynamic programming principles and the sequence and consensus maps illustrated in FIGS. 6F and 6G.

FIG. 7 shows a detailed illustration of the exemplary flow diagram and architecture of the validation procedure according to the present invention which utilizes dynamic programming principles and the sequence and consensus maps illustrated in FIGS. 6F and 6G. Each box represents the solution of a "dynamic programming"-like problem. In particular, the map data is provided to a left end table 360 which then passes at least a portion of such data to a middle table 365. The output of both the left end table 360 and the middle table 365 are combined in block 370, and the combined results are forwarded to a results table I 375. Then, at least a portion of the data from the results table I 375 is passed to a right end table 380, and the combined results are forwarded to a results table II 385. The data in the results table I 375 and the results table II 385 are computed using the scores contained in the other tables (e.g., the left end table 360, the middle table 365 and the right end table 380). The overall computation uses these three tables 360, 365, 380 as follows:

the T[.,.] for the middle table computation;
the TL[.,.] for the left end penalty computation; and
the TR[.,.] for the right end penalty computation.

It is also possible to re-use certain tables to save memory and system resources of the processing device 10. The flow of control produces the content of each table 360, 365, 380, in turn, and the final resulting table (e.g., the results table II 385) can be examined to reconstruct the alignment trace-back.

IV. Possible Optimization

Filling the entire T[.,.] table, i.e., the middle table 365, may take on the order of 4 times $O(N^2 M \min(N,M))$ to complete, where N is the size of the sequence map and M is the size of the consensus map. However, it is possible to optimize the filling of the middle table 365 down to $O(NM \min(N,M))$ by utilizing the limiting argument on the computation performed for each entry T[i, j]. Because of the limit on u and v, the computation time for each entry can be considered "constant".

In a simple setup, the middle table 365 may take up O(NM) space, hence it too may be quadratic even when extra "back-trace recording" is considered, as described in Gusfield, D., "Algorithms on Strings, Trees, and Sequences", Cambridge University Press, 1997.

It is also possible to optimize the execution time via a hashing scheme similarly to the scheme used in the "gentig" program. In such case, the time complexity can be reduced by a further order of magnitude.

Experimental Results

The first experiments using software based on the system and method described above checked "in silico" maps obtained from *Plasmodium falciparum* sequence data against optical ordered restriction maps for the same organism.

I. *Plasmodium falciparum* Sequence Data

The sequence for the *Pasmodium falciparum*'s 14 chromosomes was obtained from the Sanger Institute database (www.sanger.ac.uk) and from the TIGR database (www.tigr.org). The experiment cut the sequences "in silico" using the BamHI restriction enzyme. The resulting maps were fed to the software (implementing the process according to the present invention) along with appropriate optical ordered restriction maps.

The results of the experiments on chromosome 2 and chromosome 3 (showing a number pf fragments) are provided below, as well as the experiment on all chromosomes using a particular enzyme (e.g., NheI).

|  | Number of Fragments | |
|---|---|---|
| Chromosome | from DB | reversed |
| chr 2 | 30 | 23 |
| chr 3 | 36 | 28 |

Two "in silico" maps were provided for the chromosome 2 and chromosome 3 sequences with the fragment numbers obtained being provided in the table above. The molecule maps thus produced were then sent to the validation checker alongside various consensus maps.

II. *Plasmodium falciparum* Optical Ordered Restriction

An optical ordered restriction map published in J. Jing et al., "Optical Mapping of *Plasmodium Falciparum* Chromosome 2", Genome Research, 9:175-181, 1999 and Z. Lai et al., "A shotgun optical map of the entire *Plasmodium Falciparum* genome", Nature Genetics, 23:309-313, 1999, and the maps generated by the "gentig" program were utilized for this experiment. The "gentig" program provided the use of the indication of the overall standard deviation to be used for each fragment of the consensus map. The parameter used was:

$$\hat{\sigma} = 4.4754 \text{ Kbps},$$

and each fragment was assigned a standard deviation of:

$$\hat{\sigma}\sqrt{\frac{l}{L}}, Kbps$$

where l is the fragment size and L is the average consensus map fragment size.

III. Validation Procedure Results

The validation DPP according to the present invention was executed on chromosome 2 and chromosome 3. The DPP ran with the following limitations:

The u and v parameters for the main recurrence formula were set to 3.

The procedure for matching the left and right ends of the sequence maps using the special computations described above was not utilized.

The summary of the results are provided below in Tables 1-3. Table 1 and 3 show the match of the sequence maps for chromosomes 2 and 3 against the consensus maps generated by the "gentig". Table 2 shows the match of the sequence maps against the consensus map which as published in M. J. Gardner et al., "Chromosome 2 sequence of the human malaria parasite *Plasmodium Falciparum*", Science, 282: 1126-1132, 1998. The position of the matches of the sequence against the consensus maps are also shown in Tables 1-3.

TABLE 1

Chromosome 2 Validation Summary A

| rank | matches | score | map id | # missing cuts | # false cuts |
|---|---|---|---|---|---|
| 1 | 29 | 80.869 | 1302 | 0 | 1 |
| 2 | 28 | 105.861 | 1302 | 2 | 1 |
| 3 | 18 | 126.956 | 1326 | 12 | 4 |
| 4 | 22 | 127.488 | 1305 | 8 | 4 |
| 5 | 18 | 132.890 | 1414 | 12 | 2 |

In particular, Table 1 shows the data for the best "matches" found by the validation procedure of the present invention for the case of *Plasmodium falciparum* chromosome 2. The "in silico" sequence map was obtained from the TIGR database sequence. The sequence map (as well as its reversed) was checked against 75 (optical) consensus maps produced by the gentig program. The 75 optical maps cover the entire *Plasmodium falciparum* genome. The validation procedure located its best matches against the map tagged 1302.

TABLE 2

Chromosome 2 Validation Summary B

| rank | matches | score | map id | # missing cuts | # false cuts |
|---|---|---|---|---|---|
| 1 | 29 | 77.308 | NYU-WISC | 1 | 0 |
| 2 | 22 | 125.088 | NYU-WISC | 8 | 2 |
| 3 | 22 | 130.866 | NYU-WISC | 8 | 4 |
| 4 | 24 | 131.475 | NYU-WISC | 6 | 1 |
| 5 | 24 | 132.838 | NYU-WISC | 6 | 4 |

Table 2 shows the data for the best "matches" found by the validation procedure of the present invention for the case of *Plasmodium falciparum* chromosome 2. The "in silico" sequence map was obtained from the TIGR database sequence. The sequence map (as well as its reverse) was checked against the map published in M. J. Gardner et al. publication.

TABLE 3

Chromosome 3 Validation Summary

| rank | matches | score | map id | # missing cuts | # false cuts |
|---|---|---|---|---|---|
| 1 | 35 | 108.360 | 1365 | 1 | 0 |
| 2 | 32 | 117.571 | 1365 | 4 | 1 |
| 3 | 32 | 119.956 | 1365 | 4 | 2 |
| 4 | 35 | 121.786 | 1296 | 1 | 3 |
| 5 | 31 | 125.265 | 1365 | 5 | 1 |

Table 3 shows the data for the "best" matches found by the validation procedure of the present invention for the case of *Plasmodium falciparum* chromosome 3. The "in silico" sequence map was obtained from the Sanger Institute database sequence. The sequence map (as well as its reversed) was checked against 75 (optical) consensus maps produced by gentig. The 75 optical maps cover the entire *Plasmodium falciparum* genome. The validation procedure located its best matches against the map tagged 1365.

The processing device 10 of the present invention was executed at approximately 75×4=300 DPP instances in about 5 minutes during the experiment. Also, during this experiment, the processing device 10 kept track of all the intermediate results and made them available for interactive inspection after the actual execution. Also, the sequence, the sequence map, and the consensus maps, were always available for inspection and manipulation

IV. Conclusion

The statistical model of an exemplary embodiment of the present invention is essentially a formulation of a maximum likelihood problem which is solved by minimizing a weighted sum-of-square-error score. The solution is computed by constructing a "matching table" using a dynamic programming approach whose overall complexity is of the order $O(M \min(N, M))$ (for our non-optimized solution), where N is the length of the consensus map and M is the length of the consensus map. The preliminary results of the experiment described above illustrate how the process and system of the present invention can be used in assessing the accuracy of various sequence and map data currently being published in a variety of formats from a many different sources.

B. Alignment and Reordering Process and System

Overall Alignment Process Flow Diagram

Figure 8:
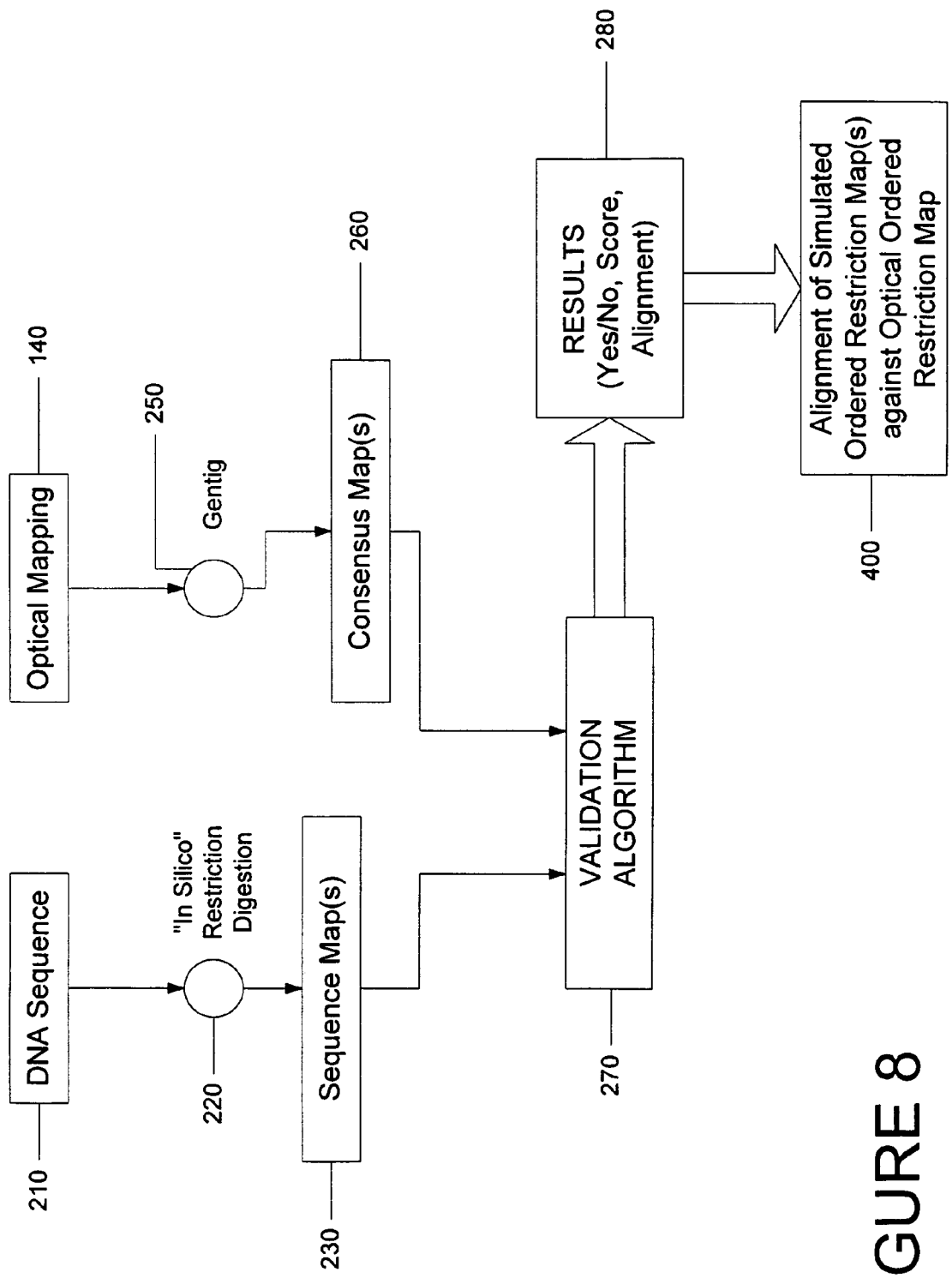
FIG. 8 is an exemplary embodiment of the process according to the present invention in which an alignment of a simulated order restricted map takes place after (or during) the validation technique has been implemented to determine the accuracy of the simulated order restricted map(s) and/or the consensus optical map(s)

FIG. 8 shows an exemplary embodiment of the process for aligning sequences using optical maps according to the present invention which can also be executed by the processing device 10 of FIGS. 1 and 2. In this exemplary embodiment and similarly to the validation process illustrated in FIG. 3, the optical mapping data 140 is forwarded to a technique 250 (e.g., the "gentig" program) which constructs one or more consensus maps 260 based on the optical mapping data 140 by considering the local variations among aligned single molecule maps.

According to this exemplary embodiment of the alignment process of the present invention, the particular DNA sequence 210 or a portion of such DNA sequence is provided. Thereafter, the data for this DNA sequence (or a portion thereof) is forwarded to a technique 220 which simulates a restriction enzyme digestion process to generate an "in silico" ordered restriction sequence map 230. The system and process of the present invention may then executes the validation algorithm 270 which determines the accuracy of the ordered restriction sequence map 230 based on the data provided in the optical consensus map(s) 260. As with the validation procedure of FIG. 3, this result can be output 280 in the form of a response a score (e.g., a rank for each ordered restriction map), a binary output (e.g., the accuracy validated vs. unvalidated), etc. The exemplary embodiments of the validation process and system of the present invention have been described in great detail herein above. Finally, the simulated ordered restriction sequence map(s) can be aligned against the optical ordered restriction map in block 400. In one exemplary embodiment of the alignment process of the present invention, for each simulated ordered restriction map, the best anchoring position of such map is located on the ordered restriction consensus map (e.g. an optical consensus map). The result of such location procedure is the generation of the entire set of anchoring positions of the simulated ordered restriction maps. In one preferred embodiment, the best anchoring positions are provided first to effectuate the best possible alignment. This can be done using a one-dimensional Dynamic Programming Procedure. Those having ordinary skill in the art would clearly understand that it is possible to produce multiple alignments for the simulated ordered restriction maps due to many anchoring positions than may be available. Provided below are further details of the alignment process and system according to the present invention.

Detailed Flow Diagram of Alignment Process

Figure 9:
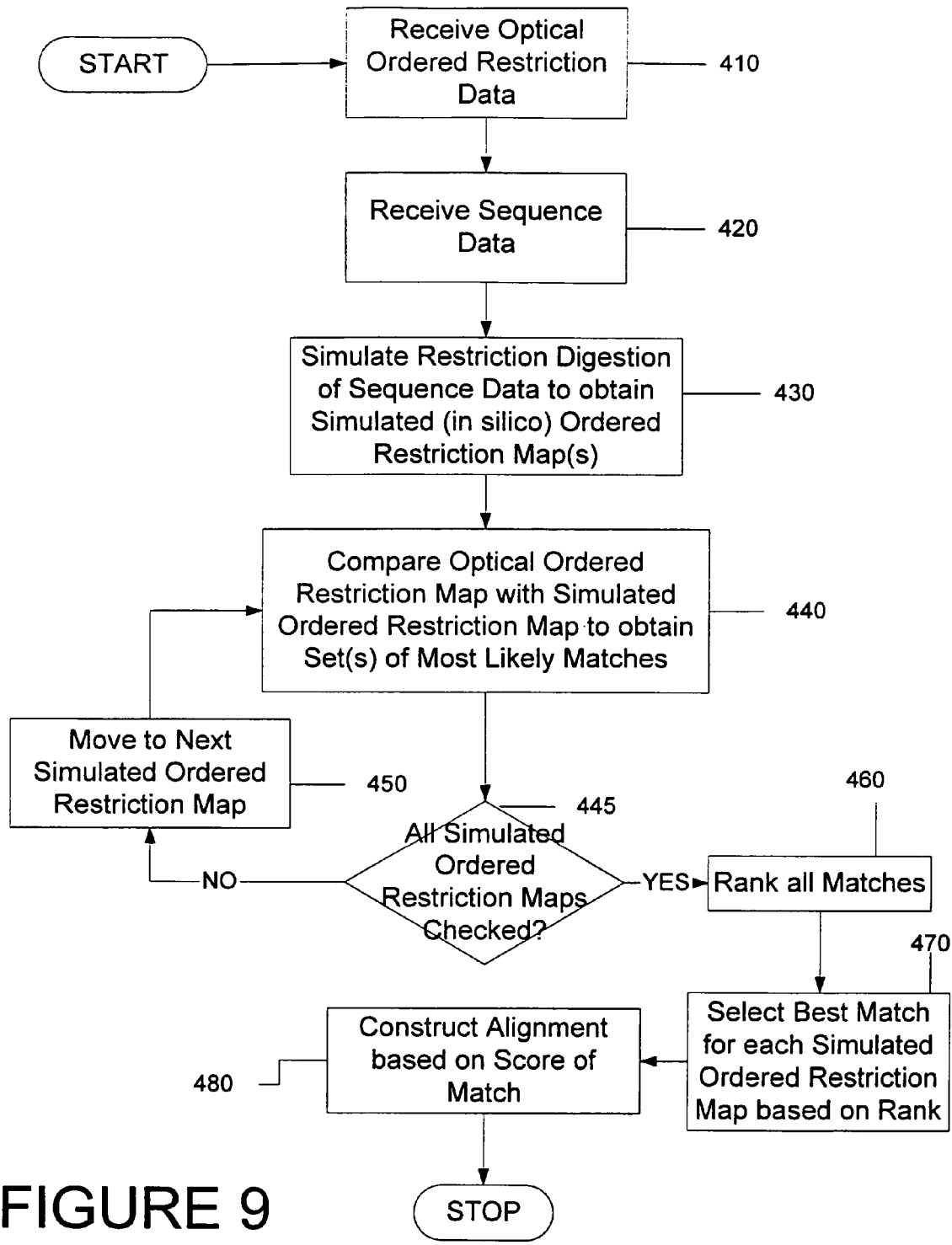
FIG. 9 is a detailed illustration of the flow diagram of the process show in FIG. 8.

FIG. 9 shows an exemplary flow chart of the embodiment of the process according to the present invention for simulating a restriction digestion of the sequence map, validating the accuracy of the consensus optical order restriction map and/or the simulated map, and constructing an alignment therefore. This process can be performed by the processing device 10 which is shown in FIGS. 1 and 2. Similarly to the validation process shown in FIG. 4, the processing device 10 receives the optical ordered restriction data in step 410, which can be the consensus optical map(s) 260 shown in FIG. 8. Then, in step 420, the processing device 10 receives the sequence data, which is preferably the DNA sequence data 210 also shown in FIG. 8. In step 430, the restriction digestion of the sequence data is simulated to obtain the simulated (in silico) ordered restriction map which is also shown in FIG. 8 as the sequence map(s) 230. Thereafter, the optical ordered restriction map is compared to the simulated ordered restriction map to obtain one or more sets of most likely matches (step 440). The processing device 10 then determines if all the simulated ordered restriction maps were checked in step 445.

If not, the process takes the next simulated ordered restriction map to be the current simulated ordered restriction map to be checked in step 450, and the comparison of step 440 is repeated again for the current simulated ordered restriction map. Otherwise, since it is determined that all the simulated ordered restriction maps were checked, all of the matches are ranked in step 460, and the processing device 10 determines the best match(es) for each simulated ordered restriction map based on the respective ranks in step 470. Then, in step 480, the alignment of the simulated ordered restriction map is constructed with respect to the optical ordered restriction maps based on the score of the matches.

Global Alignment

To reiterate, the validation process and system of the present invention described above can match an ordered restriction sequence map against an ordered restriction consensus map. This validation process and system can be possibly described as a positioning process of the sequence map against the consensus map. When many sequences positioning are taken into consideration, it may be possible to describe the validation process as a "global" collective alignment against a particular consensus map. Thus, for the sake of clarity, the output of the procedure that produces this final result shall be referred to herein below as an alignment.

For example, the result of n "validation experiments" can be identified as n sets of possible sequence positions along the consensus map. Each of these results can be denoted as set $S_i$ (with $0<i\leq n$), with $|S_i|=k$. Each of the k items in each $S_i$ is a triple $[s_i, x_{(i,j)}, v_{(i,j)}]$—where $S_i$ is a sequence map identifier, $x_{(i,j)}$ is the j-th alignment of $s_i$ against the consensus map, and $v_{(i,j)}$ is the sequence alignment score (with $0<j\leq k$) obtained from the single sequence (map) positioning process. The set containing every $S_i$ (with $0<i\leq n$) is called S.

Figure 10:
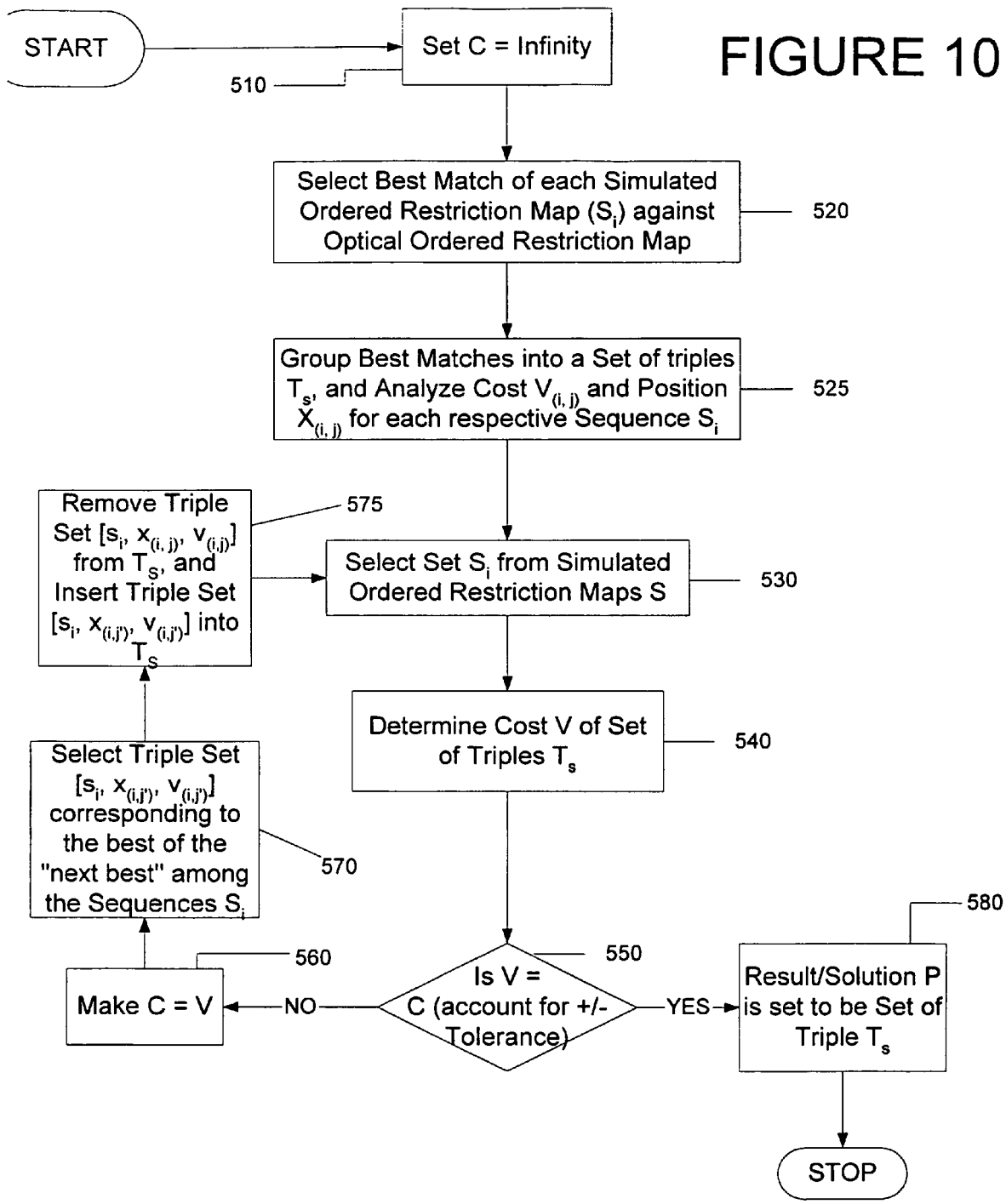
FIG. 10 is a flow diagram of a particular set of steps in the process illustrated in FIG. 9 in which best matches are selected for each sequence map and an overall alignment thereof is constructed.

An exemplary embodiment of the procedure to perform the matching, ranking and alignment steps 440-480 using the sequence maps and costs described above is provided below with reference to FIG. 10. The end result will preferably be an alignment whose overall cost C can be computed by summing all the costs $v_{(i,j)}$ eventually selected.

Initially, in step 510, the global cost C is set to infinity. Then, in step 520, the best matches out of each set $S_i$ of simulated ordered restriction maps (i.e., sequence maps) against the optical ordered restriction map (i.e., the consensus map) are selected. The best matches are grouped into a set of triples called $T_S$, and the cost $v(i, j)$ and the position $x_{(i,j)}$ of each respective sequence $S_i$ are analyzed in step 525. A set, $S_i$, is selected from the simulated ordered restriction map S in step 530. The cost V of this set of triples $T_S$ is then computed using, e.g., a specialized 1D Dynamic Programming Procedure (step 540), and compared to C. If V is equal to C plus or minus a tolerance value (step 550), then the set of triples $T_S$ is determined to be the result of the alignment procedure (step 580). If V is not equal to C plus or minus a tolerance value, then first C is equated to V at step 560, and the triple $[s_i, x_{(i,j')}, v_{(i,j')}]$ corresponding to the best of the "second best" among the $S_i$'s is selected (step 570). The triple $[s_i, x_{(i,j)}, v_{(i,j)}]$ is then removed from the set of triples $T_S$, and the triple $[s_i, x_{(i,j')}, v_{(i,j')}]$ (with j different from j') is inserted into the set of triples $T_S$ (step 575). A set $S_i$ is again selected at step 530. A new V is then computed from the updated set of triples $T_S$ (step 540).

Provided below is an exemplary map-based alignment algorithm/problem which can be utilized with the alignment process and system of the present invention. Let $S=\cup_i S_i$. For example, at most one triple from each $S_i$, can be selected while satisfying the following global conditions/objectives which can possibly be relaxed:

1. When anchoring two or more selected triples within the alignment $T_S$, two selected sequences $s_p$ and $s_q$ anchored at their respective $x_{(p,b)}$ and $x_{(q,a)}$, preferably do not overlap (for suitable p, q, a, and b and p not equal to q);
2. $\Sigma(I_i \times v_{(i,j)})$ is minimized over each j in the sequences set $S_i$ so that as many as possible sequence maps $S_i$'s are included in the alignment; and
3. the number of non-selected sequences, $n-\Sigma_i I_i$ is minimized.

where $I_i$ is an indicator variable assuming a value 1 if the triplet from the sequence $S_i$ is included in the chosen set $T_S$, and 0 otherwise.

It should be understood that the objectives (2) and (3) provided above may conflict. In particular, the minimum of the objective (2) is achieved when no sequence is selected, while with the objective (3), it is preferable to choose as many sequences as possible, irrespective of the score values. This conflict may be resolved by, e.g., a weighting scheme involving a Lagrangian-like term which linearly combines the two contradictory objectives.

It is possible to solve this problem by using various approximation algorithms. For example, the following two algorithms/procedures:

1. a "Greedy" algorithm/procedure, and
2. a "Dynamic Programming" algorithm/procedure.

During the experimentation of the alignment system and process of the present invention, the Greedy algorithm/procedure and the Dynamic Programming algorithm/procedure were utilized with successful results. Provided below are the detailed description of these algorithms/procedures (1)-(2) of the present invention.

Greedy Algorithm/Procedure

A solution P can be constructed such that each $S_i$ is ordered by value $v_{(i,j)}$. Then, the best item from each sequence $S_i$ is placed in the partial solution P by selecting the sequences in the order imposed by each $x_{(i,j)}$. It should be understood that the final solution P is not guaranteed to be optimal; however, this solution may provide the results which may be acceptable to the implementers of the alignment procedures.

Dynamic Programming/Procedure

This algorithm/procedure is based on the traditional dynamic programming approach. Indeed, the implementation of this algorithm/procedure is straight forward and space-efficient as provided below. The problem can first be considered for one exemplary case when k=1, and an appropriate algorithm can be selected. Next, the general case when k>1 can be considered, and good approximation heuristics may be devised.

(a) Alignment procedure for Sequence number k being 1. If the number of sequences k present in each set $S_i$ of triples is restricted to be 1 (e.g., being the best score), then the problem yields to a feasible and efficient algorithm. In general, if the sequence matches uniquely to one map location, then this case should apply. An exemplary embodiment of the alignment algorithm for the dynamic programming solution, constructing the solution P, is described below. In particular, 1. Sort all the triples of sequence, cost and position, $<s_i, x_{(i,j)}, v_{(i,j)}>$ in ascending $x_{(i,j)}$ order, and store the result in a list L. Thereafter, the indices i and j can be assumed to range over the list L.
2. Construct two vectors C[i] and B[i] ($0<i\leq n$), where each entry in global cost C is defined to be the cost of including si in an alignment that already contains sequences, or a subset thereof, up to $S_j$; and the index j is stored in B[i].

The update rules for C[i] and B[i] preferably search backward in the C vector for values which minimize the cost function, and set B to "point back" to the chosen point. For example, $C[i]=\max(C[j]+W(\lambda;i))$ such that $S_i$ does not overlap with $S_j$, $0<j<i$ $B[i]=j$.

$W(\lambda; i)$ function takes into consideration the conflicting nature of the objectives described above. Since it is most likely not possible to optimize both objectives simultaneously, a weight function can be generated (where a user may supply the parameter $\lambda$) which would preferably account for both objectives. Two exemplary W functions are provided below:

$W_1(\lambda;i)=|S_i|-\lambda \cdot v_i$, $W_2(\lambda;i)=1-\lambda \cdot v_i$.

$W_1$ takes into account the "span" covered by the selected sequences (where $|S_i|$ is the size of the sequence). $W_2$ takes into account the number of sequences which were selected. The parameter $\lambda$ is controlled by the user.

(b) Alignment Procedure for Sequence Number k>1. If sequence number k>1, then the procedure may be more complex. Since for each set $S_i$, there may be k number of alignments to select from, the complexity involved in a straightforward generalization of the preceding procedure is conjectured to grow exponentially. It is possible to use a heuristic procedure/algorithm to produce an acceptable solution in the case when the sequence number k>1. The concept of this procedure is to iterate or repeat the dynamic programming procedure (i.e., k=1 case) on an input set that takes the best possible solutions from each sequence $S_i$ while ignoring the non-overlapping constraint. This solution can be further improved in the subsequent iteration by constructing a new input to the DPP procedure (i.e., where k=1) that consists of the preceding solution augmented with an element from each sequence $S_i$ excluded in the preceding solution. Because the preceding solution is also a solution of the new expression, the new solution is at least as effective as the solution previously provided. In each iteration, the basic solution can also be a general (and possibly suboptimal) solution. Because when an item is removed from consideration, it is never again reconsidered; thus, according to a preferred embodiment of the present invention, there can be only O(kn) iterations, and each iteration involves $O(n^2)$ work. Hence a naive analysis yields an $O(kn^3)$ time algorithm.

Experimental Results

Figure 11:
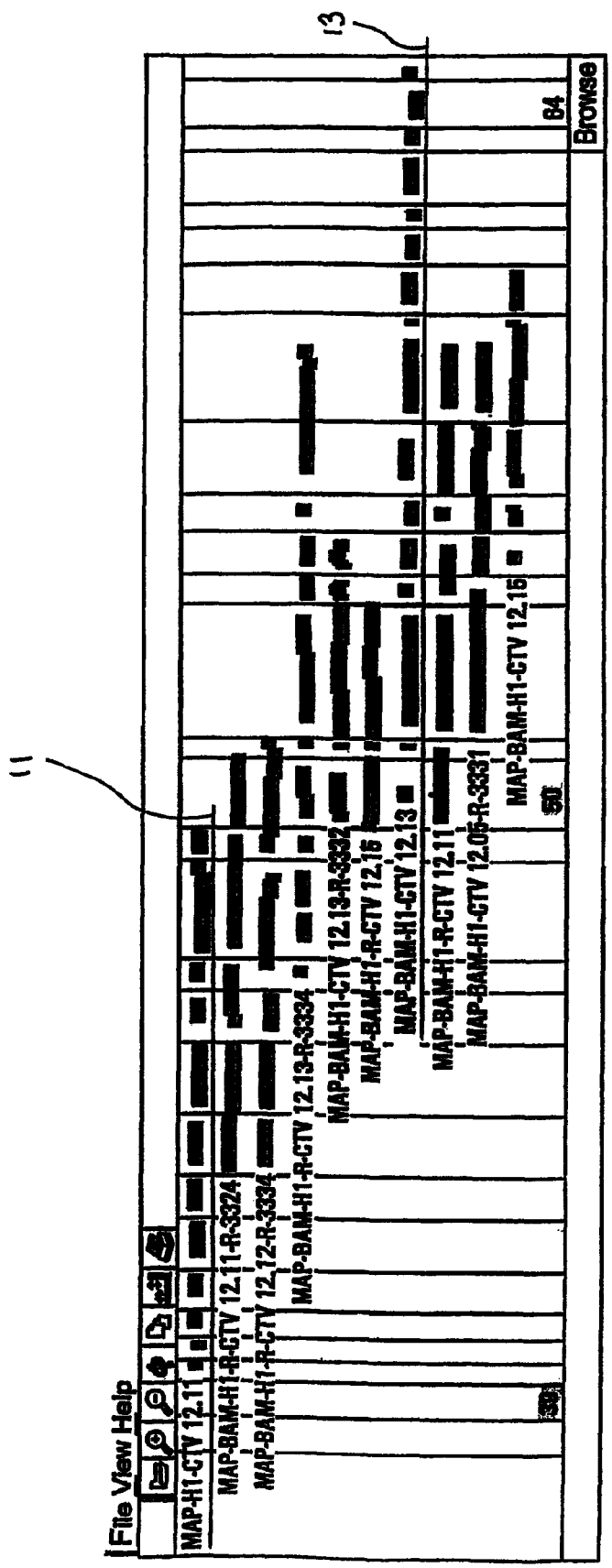
FIG. 11 is an illustration of an example of a possible alignment of a chromosome arrangement using the system and process of the present invention.

FIG. 11 shows an illustration of a possible alignment of an exemplary chromosome arrangement using the system and method of the present invention. In particular, a region of the alignment of *P. falciparum*'s Chromosome 12 is shown therein which was generated using the software implementing an exemplary embodiment of the validation, alignment and reordering system and method of the present invention. The two underlined maps in position 39 and 50 of the figure illustrate an acceptable anchoring of "contigs" 11 and 13 to the optical ordered restricted map. Also, the alignment was obtained without any overlap filter.

One having ordinary skill in the art would clearly recognize that many other applications of the embodiments of the system and process for validating and aligning of the simulated ordered restriction maps according to the present invention. Indeed, the present invention is in no way limited to the exemplary applications and embodiments thereof described above.

The invention claimed is:

1. A process for comparing ordered segments of a first DNA map with ordered segments of a second DNA map to determine a level of accuracy of the second DNA map with respect to the first DNA map, comprising the steps of:
   a) receiving in a processing device the first and second DNA maps, wherein the first DNA map is a sequence DNA map generated by cutting a DNA molecule using one or more restriction enzymes, and the second DNA map is a genomic consensus DNA map in an ordered restriction DNA map; and
   b) validating in the processing device the level of accuracy of and the second DNA map with respect to the first DNA map based on information associated with the first and second DNA maps by comparing ordered segments of the first DNA map with ordered segments of the second DNA map using the following probability density function:

$Pr(D|\hat{H}(\sigma,p_c,p_f))$ where:
   D is the second DNA map,
   $\hat{H}$ is the first DNA map,
   $\sigma$ is a standard deviation summarizing map-wide standard deviation data,
   $p_c$ is a probability of a positive cut of a DNA sequence, and
   $p_f$ is a probability of a false-positive cut of the DNA sequence,
   whereby a level of accuracy the second DNA map with respect to the first DNA map is determined.

2. The process according to claim 1, wherein the validating step comprises determining whether one or more matches exist between the ordered segments of the first DNA map and the ordered segments of the second DNA map.

3. The process according to claim 2, wherein the validating step further comprises obtaining a number of the matches which exist between the ordered segments of the first DNA map and the ordered segments of the second DNA map after determining whether one or more matches exist between ordered segments of the first DNA map and the ordered segments of the second DNA map.

4. The process according to claim 3, wherein the validating step further comprises the substeps of:
   i. determining whether the first DNA map includes one or more cuts which are missing from the second DNA map,
   ii. after substep i, obtaining a first number and locations of the missing cuts based on the first and second DNA maps,
   iii. determining whether the second DNA map includes one or more cuts which are missing from the first DNA map, and
   iv. after substep iii, obtaining a second number and locations of the missing cuts based on the first and second DNA maps.

5. The process according to claim 4, further comprising the step of:
   c) generating an error indication if at least one of:
      i. the number of the matches is less than a match threshold,
      ii. the first number of the missing cuts is greater than a first predetermined threshold, and
      iii. the second number of the missing cuts is greater than a second predetermined threshold.

6. The process according to claim 1, wherein the validating step comprises determining whether the first DNA map includes one or more cuts which are missing from the second DNA map.

7. The process according to claim 6, wherein the validating step further comprises obtaining a number and locations of the missing cuts, after determining whether one or more matches exist between ordered segments of the first DNA map and the ordered segments of the second DNA map, based on the first and second DNA maps.

8. The process according to claim 1, wherein the validating step comprises determining whether the second DNA map includes one or more cuts which are missing from the first DNA map.

9. The process according to claim 8, wherein the validating step further comprises obtaining a number and locations of the missing cuts, after determining whether one or more matches exist between ordered segments of the first DNA map and the ordered segments of the second DNA map, based on the first and second DNA maps.

10. The process according to claim 1, wherein the first DNA map is an in-silico ordered restriction map obtained from a DNA sequence.

11. The process according to claim 10, wherein the first DNA map includes identification data and at least one vector of the segments of the first DNA map.

12. The process according to claim 11, wherein the at least one vector of the first segments encodes a size of base-pairs of the DNA sequence.

13. The process according to claim 12, wherein the second DNA map includes identification data and at least one variable-length vector representing its ordered segments.

14. The process according to claim 1, wherein the second DNA map is a subsequence of a genome-wide ordered restriction map of an optical DNA map.

15. The process according to claim 1, wherein the level of accuracy is validated as a function of an orientation of the first DNA map with respect to an orientation of the second DNA map.

16. The process according to claim 1, wherein the validation step comprises the substeps of:
   i. executing a dynamic programming procedure ("DPP") on the first and second DNA maps to generate a first table of partial and complete alignment scores, and first auxiliary tables and first data structures to keep track of number and locations of cuts and segment matches, wherein the DPP comprises:
   assembling a N×M matching table T, wherein index "i" indicates a fragment in a consensus map having M fragments and index "j" indicates a fragment in a sequence map having N fragments, wherein each entry of the matching table T is computed by $$T[i, j] = \min_{\substack{0 < u \leq i \\ 0 < v \leq j}} \left\{ \begin{array}{l} T[i-u, j-v] + \\ \ln\left(\dfrac{\sqrt{2\pi(\sigma_i^2 + \sigma_{(i-1)}^2 + \ldots + \sigma_{(i-v)}^2)}}{p_c}\right) + \\ \dfrac{((l_i + l_{(i-1)} + \ldots + l_{(i-v)}) - (a_j + a_{(j-1)} + \ldots + a_{(j-u)}))^2}{2(\sigma_i^2 + \sigma_{(i-1)}^2 + \ldots + \sigma_{(i-v)}^2)} + \\ (u-1)\ln\dfrac{1}{1-p_c} + \\ (v-1)\ln\dfrac{1}{p_f} \end{array} \right\}$$

wherein "u" is a given cut in the sequence map, "v" is a given cut in the consensus map, "$p_c$" is the probability of a positive cut in the sequence map, "$p_f$" is the probability of a false-positive cut in the sequence map, "1" is the fragment length, and "$\sigma_i$" is the estimated standard deviation of fragment sizes, ii. receiving a third DNA map which is a reverse map of the first DNA map,
   iii. executing the DPP on the second and third DNA maps to generate a second table of partial and complete alignment scores, and second auxiliary tables and second data structures to keep track of number and locations of the cuts and the segment matches, and
   iv. analyzing a last row of the first table and a last row of the second table to obtain at least one optimum alignment of the first and second DNA maps, and
   v. constructing at least one of the optimum alignment and suboptimal alignments using the first and second auxiliary tables and data structures.

17. The process according to claim 1, wherein the level of accuracy is validated by matching an extension of a first left end segment of the ordered segments of the first DNA map to at least one of the ordered segments of the second DNA map.

18. The process according to claim 1, wherein the level of accuracy is validated by matching an extension of a first right end segment of the ordered segments of the first DNA map to at least one of the ordered segments of the second DNA map.

19. The process according to claim 1, further comprising the step of:
   c) detecting an alignment of the first DNA map with respect to the second DNA map, the alignment being indicative of sequence positions of the ordered segments of the first DNA map along the second DNA map.

20. A software system which, when executed on a processing device, configures the processing device to compare segments of a first DNA map with segments of a second DNA map to determine a level of accuracy of the second DNA map with respect to the first DNA map, the software system comprising:
   a processing device;
   a processing subsystem stored in the processing device and which, when executed on the processing device, configures the processing device to perform the following steps:
   a) receives the first and second DNA maps, wherein the first DNA map is a sequence DNA map generated by cutting a DNA molecule using one or more restriction enzymes, and the second DNA map is a genomic consensus DNA map in an ordered restriction DNA map,
   b) validates the level of accuracy of the second DNA map with respect to the first DNA map based on information associated with the first and second DNA maps by comparing ordered segments of the first DNA map with ordered segments of the second DNA map using the following probability density function:

$$\Pr(D|\hat{H}(\sigma, p_c, p_f))$$

where:
   D is the second DNA map,
   $\hat{H}$ is the first DNA map,
   $\sigma$ is a standard deviation summarizing map-wide standard deviation data,
   $p_c$ is a probability of a positive cut of a DNA sequence, and
   $p_f$ is a probability of a false-positive cut of the DNA sequence, whereby a level of accuracy of the second DNA map with respect to the first DNA map is determined, and c) outputs the level of accuracy to a user.

21. The software system according to claim 20, wherein, when validating the level of accuracy, the processing subsystem determines whether one or more matches exists between at least one of the segments of the first DNA map and at least one of the segments of the second DNA map.

22. The software system according to claim 21, wherein, when validating the level of accuracy, the processing subsystem obtains a number of the matches which exist between the segments of the first DNA map and the segments of the second DNA map after determining whether one or more matches exist between the ordered segments of the first DNA map and the ordered segmetns of the second DNA map.

23. The software system according to claim 22, wherein, when validating the level of accuracy, the processing subsystem:
   i. determines whether the first DNA map includes one or more cuts which are missing from the second DNA map,
   ii. obtains number and location of the missing cuts based on the first and second DNA maps,
   iii. determines whether the second DNA map includes one or cuts which are missing from the first DNA map, and
   iv. obtains a second number of the missing cuts based on the first and second DNA maps.

24. The software system according to claim 23, wherein, when executed on the processing device, the processing subsystem further configures the processing device to generate an error indication if at least one of:
   i. the number of the matches is less than a match threshold,
   ii. the first number of the missing cuts is greater than a first predetermined threshold, and
   iii. the second number of the missing cuts is greater than a second predetermined threshold.

25. The software system according to claim 20, wherein, when validating the level of accuracy, the processing subsystem determines whether the first DNA map includes one or more cuts which are missing from the second DNA map.

26. The software system according to claim 25, wherein, when validating the level of accuracy, the processing subsystem obtains number and location of the missing cuts based on the first and second DNA maps.

27. The software system according to claim 20, wherein, when validating the level of accuracy, the processing subsystem obtains number and location of the missing cuts, after determining whether one or more matches exist between ordered segments of the first DNA map and the ordered segments of the second DNA map, based on the first and second DNA maps.

28. The software system according to claim 20, wherein, when validating the level of accuracy, the processing subsystem determines whether the second DNA map includes one or more cuts which are missing from the first DNA map.

29. The software system according to claim 20, wherein the first DNA map is an in-silico ordered restriction map obtained from a DNA sequence.

30. The software system according to claim 29, wherein the first DNA map includes identification data and a variable-length vector of the segments of the first DNA map.

31. The software system according to claim 30, wherein the vector of the segments of the first DNA map encodes a size of base pairs of the DNA sequence.

32. The software system according to claim 31, wherein the second DNA map includes identification data and a variable length vector of the segments of the second DNA map.

33. The software system according to claim 20, wherein the second DNA map is a genome-wide ordered restriction map of an optical DNA map.

34. The software system according to claim 20, wherein the level of accuracy is validated as a function of an orientation of the first DNA map with respect to an orientation of the second DNA map.

35. The software system according to claim 20, wherein, when validating the level of accuracy, the processing subsystem:

i. executes a dynamic programming procedure ("DPP") on the first and second DNA maps to generate a first table of partial and complete alignment scores, and first auxiliary tables and data structures to keep track of number and locations of cuts and segment matches, wherein the DPP comprises:

assembling a N×M matching table T, wherein index "i" indicates a fragment in a consensus map having M fragments and index "j" indicates a fragment in a sequence map having N fragments, wherein each entry of the matching table T is computed by $$T[i, j] = \min_{\substack{0 < u \le i \\ 0 < v \le j}} \left\{ \begin{array}{l} T[i-u, j-v] + \\ \ln\left(\dfrac{\sqrt{2\pi(\sigma_i^2 + \sigma_{(i-1)}^2 + \ldots + \sigma_{(i-v)}^2)}}{p_c}\right) + \\ \dfrac{((l_i + l_{(i-1)} + \ldots + l_{(i-v)}) - (a_j + a_{(j-1)} + \ldots + a_{(j-u)}))^2}{2(\sigma_i^2 + \sigma_{(i-1)}^2 + \ldots + \sigma_{(i-v)}^2)} + \\ (u-1)\ln\dfrac{1}{1-p_c} + \\ (v-1)\ln\dfrac{1}{p_f} \end{array} \right\}$$

wherein "u" is a given cut in the sequence map, "v" is a given cut in the consensus map, "$p_c$" is the probability of a positive cut in the sequence map, "$p_f$" is the probability of a false-positive cut in the sequence map, "1" is the fragment length, and "$\sigma_i$" is the estimated standard deviation of fragment sizes, ii. receives a third DNA map which is a reverse map of the first DNA map, iii. executes the DPP on the second and third DNA maps to generate a second table of partial and complete alignment scores, and second auxiliary tables and data structures to keep track of number and locations of cuts and segment matches, iv. analyzes a last row of the first table and a last row of the second table to obtain at least one optimum alignment of the first and second DNA maps, and v. constructing at least one of the optimum alignment and suboptimal alignments using the first and second auxiliary tables and data structures.

36. The software system according to claim 20, wherein the level of accuracy is validated by matching an extension of a first left end segment of the segments of the first DNA map to at least one of the segments of the second DNA map.

37. The software system according to claim 20, wherein the level of accuracy is validated by matching an extension of a first right end segment of the first DNA map to at least one of the segments of the second DNA map.

38. The software system according to claim 20, wherein, when executed on the processing device, the processing subsystem further configures the processing device to determine an alignment of the first DNA map with respect to the second DNA map, the alignment being indicative of sequence positions of the first segments along the second DNA map.

* * * * *

UNITED STATES PATENT AND TRADEMARK OFFICE
CERTIFICATE OF CORRECTION

PATENT NO. : 7,831,392 B2  
APPLICATION NO. : 10/432766  
DATED : November 9, 2010  
INVENTOR(S) : Marco Antoniotti et al.

Page 1 of 1

It is certified that error appears in the above-identified patent and that said Letters Patent is hereby corrected as shown below:

In the Specification

Column 1, line 7, please insert:

--STATEMENT REGARDING FEDERALLY SPONSORED RESEARCH

This invention was made with government support under DE-FG02-00ER62917 awarded by the US Department of Energy. The government has certain rights in the invention.--

Signed and Sealed this
Seventeenth Day of September, 2013

Teresa Stanek Rea
*Deputy Director of the United States Patent and Trademark Office*